United States Patent
Thompson et al.

(10) Patent No.: US 10,959,958 B2
(45) Date of Patent: Mar. 30, 2021

(54) EXTENDED RELEASE ABUSE DETERRENT LIQUID FILL DOSAGE FORM

(71) Applicant: Pharmaceutical Manufacturing Research Services, Inc., Horsham, PA (US)

(72) Inventors: Edwin R. Thompson, Horsham, PA (US); Eric R. Thompson, Chalfont, PA (US); Nicholas R. Myslinski, Bensalem, PA (US); Steven F. Kemeny, Philadelphia, PA (US); Matthew N. Hart, Palmyra, NJ (US)

(73) Assignee: Pharmaceutical Manufacturing Research Services, Inc., Horsham, PA (US)

( * ) Notice: Subject to any disclaimer, the term of this patent is extended or adjusted under 35 U.S.C. 154(b) by 0 days.

(21) Appl. No.: 15/175,377

(22) Filed: Jun. 7, 2016

(65) Prior Publication Data

US 2017/0020822 A1  Jan. 26, 2017

Related U.S. Application Data

(62) Division of application No. 14/918,112, filed on Oct. 20, 2015, now abandoned.

(60) Provisional application No. 62/066,298, filed on Oct. 20, 2014.

(51) Int. Cl.
*A61K 9/48* (2006.01)
*A61K 31/485* (2006.01)

(52) U.S. Cl.
CPC .......... *A61K 9/4866* (2013.01); *A61K 9/4858* (2013.01); *A61K 31/485* (2013.01)

(58) Field of Classification Search
CPC .................................................. A61K 31/485
See application file for complete search history.

(56) References Cited

U.S. PATENT DOCUMENTS

| | | |
|---|---|---|
| 3,439,089 A | 4/1969 | Cherkas et al. |
| 4,450,877 A | 5/1984 | Walker et al. |
| 5,141,961 A | 8/1992 | Coapman |
| 5,202,128 A | 4/1993 | Morella et al. |
| 5,266,331 A | 11/1993 | Oshlack et al. |
| 5,431,916 A | 7/1995 | White |
| 5,458,879 A | 10/1995 | Singh et al. |
| 5,614,218 A | 3/1997 | Olsson et al. |
| 5,616,621 A | 4/1997 | Popli et al. |
| 5,827,852 A | 10/1998 | Russell et al. |
| 5,840,337 A | 11/1998 | Cody et al. |
| 5,840,731 A | 11/1998 | Mayer et al. |
| 5,866,164 A | 2/1999 | Kuczynski et al. |
| 5,914,129 A | 6/1999 | Mauskop |
| 6,024,980 A | 2/2000 | Hoy |
| 6,068,855 A | 5/2000 | Leslie et al. |
| 6,102,254 A | 8/2000 | Ross |
| 6,159,501 A | 12/2000 | Skinhoj |
| 6,160,020 A | 12/2000 | Ohannesian et al. |
| 6,190,591 B1 | 2/2001 | van Lengerich |
| 6,207,674 B1 | 3/2001 | Smith |
| 6,245,357 B1 | 6/2001 | Edgren et al. |
| 6,251,430 B1 | 6/2001 | Zhang et al. |
| 6,277,384 B1 | 8/2001 | Kaiko et al. |
| 6,309,669 B1 | 10/2001 | Setterstrom et al. |
| 6,432,450 B1 | 8/2002 | Gergely et al. |
| 6,488,963 B1 | 12/2002 | McGinity et al. |
| 6,500,459 B1 | 12/2002 | Chhabra et al. |
| 6,572,891 B1 | 6/2003 | Ugarkovic |
| 6,627,635 B2 | 9/2003 | Palermo et al. |
| 6,706,281 B2 | 3/2004 | Oshlack et al. |
| 6,713,470 B2 | 3/2004 | Jackson |
| 6,740,333 B2 | 5/2004 | Beckett et al. |
| 6,753,009 B2 | 6/2004 | Luber et al. |
| 6,800,668 B1 | 10/2004 | Odidi et al. |
| 6,869,618 B2 | 3/2005 | Kiel et al. |
| 6,905,709 B2 | 6/2005 | Oshlack et al. |
| 6,923,988 B2 | 8/2005 | Patel et al. |
| 7,141,250 B2 | 11/2006 | Oshlack et al. |
| 7,201,920 B2 | 4/2007 | Kumar et al. |
| 7,214,385 B2 | 5/2007 | Gruber |
| 7,316,821 B2 | 1/2008 | Oshlack et al. |
| 7,384,653 B2 | 6/2008 | Wright, IV et al. |
| 7,413,750 B2 | 8/2008 | Kolter et al. |
| 7,514,100 B2 | 4/2009 | Oshlack et al. |

(Continued)

FOREIGN PATENT DOCUMENTS

| | | |
|---|---|---|
| CA | 264736 A | 10/1926 |
| CA | 265145 A | 10/1926 |

(Continued)

OTHER PUBLICATIONS

Cole. Liquid Filled and Sealed Hard Gelatin Capsules 2000.*
Mohsin et al. Suitability of Gelucire®50/13 for Controlled Release Formulation of Salbutamol Sulphate. Jan. 2012.*
Worker B. Beeswax Ingredients. Feb. 2011.*
"Poloxamer" from Wikipedia, the free encyclopedia—4 Pages.
Gazzaniga et al., "A novel injection-molded capsular device for oral pulsatile delivery based on swellable/erodible polymers", AAPS PharmSciTech, 2011, vol. 12, No. 1, pp. 295-303.
Soininen et al., "Effect of polyethylene glycol 20000 on bioavailability of micronized and crystalline paracetamol", Acta Pharmaceutica Fennica, 1981, vol. 90, vol. 4, pp. 381-386.
Soininen et al., "Dissolution rate of different kinds of granulated micronized paracetamol with adjuvant incorporated either inter- or intragranularly", Acta Pharmaceutica Fennica, 1981, vol. 90. No. 2, pp. 153-162.

(Continued)

*Primary Examiner* — Sarah Alawadi
(74) *Attorney, Agent, or Firm* — McCarter & English, LLP; Yu Lu

(57) ABSTRACT

The present disclosure relates to an oral, extended release, abuse deterrent dosage form containing a controlled release agent, a second agent and/or polyethylene glycol, and at least one active pharmaceutical ingredient susceptible to abuse. The dosage form is stable at high temperatures and abuse deterrent to oral and parenteral administration via dose dumping, extraction, and purification. The present disclosure also relates to processes of preparing the dosage form.

18 Claims, 7 Drawing Sheets

(56) References Cited

U.S. PATENT DOCUMENTS

| | | |
|---|---|---|
| 7,544,676 B2 | 6/2009 | Dolle et al. |
| 7,655,256 B2 | 2/2010 | Hughes |
| 7,666,337 B2 | 2/2010 | Yang et al. |
| 7,670,612 B2 | 3/2010 | Miller |
| 7,670,627 B2 | 3/2010 | Shefer et al. |
| 7,718,194 B2 | 5/2010 | Chenevier et al. |
| 7,744,916 B2 | 6/2010 | Pauletti et al. |
| 7,754,240 B2 | 7/2010 | Staniforth et al. |
| 7,780,987 B2 | 8/2010 | Zhou et al. |
| 7,790,215 B2 | 9/2010 | Sackler et al. |
| 7,842,307 B2 | 11/2010 | Oshlack et al. |
| 7,846,460 B2 | 12/2010 | Chenevier et al. |
| 7,846,476 B2 | 12/2010 | Oshlack et al. |
| 7,910,128 B2 | 3/2011 | Chang et al. |
| 7,943,173 B2 | 5/2011 | Breder et al. |
| 7,968,119 B2 | 6/2011 | Farrell |
| 8,029,822 B2 | 10/2011 | Faour et al. |
| 8,075,872 B2 | 12/2011 | Arkenau-Maric et al. |
| 8,114,383 B2 | 2/2012 | Bartholomaus et al. |
| 8,124,126 B2 | 2/2012 | Bosse et al. |
| 8,133,507 B2 | 3/2012 | Yum et al. |
| 8,138,169 B2 | 3/2012 | Oronsky et al. |
| 8,143,267 B2 | 3/2012 | Burch et al. |
| 8,188,108 B2 | 5/2012 | Mayo-Alvarez et al. |
| 8,202,542 B1 | 6/2012 | Mehta et al. |
| 8,216,610 B2 | 7/2012 | Roberts et al. |
| 8,263,125 B2 | 9/2012 | Vaya et al. |
| 8,313,757 B2 | 11/2012 | van Lengerich |
| 8,318,105 B2 | 11/2012 | Selinfreund et al. |
| 8,318,641 B2 | 11/2012 | Selinfreund et al. |
| 8,333,989 B2 | 12/2012 | Sukuru |
| 8,337,888 B2 | 12/2012 | Wright et al. |
| 8,362,029 B2 | 1/2013 | Evenstad et al. |
| 8,377,453 B2 | 2/2013 | Han et al. |
| 8,383,152 B2 | 2/2013 | Jans et al. |
| 8,394,813 B2 | 3/2013 | Mickle et al. |
| 8,415,401 B2 | 4/2013 | Yum et al. |
| 8,420,114 B2 | 4/2013 | Zanella et al. |
| 8,426,411 B2 | 4/2013 | Wishart et al. |
| 8,445,023 B2 | 5/2013 | Guimberteau et al. |
| 8,465,776 B2 | 6/2013 | Hoarau |
| 8,481,560 B2 | 7/2013 | Stinchcomb et al. |
| 8,486,448 B2 | 7/2013 | Rahmouni et al. |
| 8,486,449 B2 | 7/2013 | Rahmouni et al. |
| 8,497,303 B2 | 7/2013 | Wurn et al. |
| 8,501,160 B2 | 8/2013 | Cailly-Dufestel et al. |
| 8,518,438 B2 | 8/2013 | Rashid et al. |
| 8,524,267 B2 | 9/2013 | Zanella et al. |
| 8,563,038 B2 | 10/2013 | Andersen et al. |
| 8,575,196 B2 | 11/2013 | Riggs-Sauthier et al. |
| 8,591,947 B2 | 11/2013 | Vergez et al. |
| 8,597,681 B2 | 12/2013 | Park et al. |
| 8,603,514 B2 | 12/2013 | Yang et al. |
| 8,603,525 B2 | 12/2013 | Oury et al. |
| 8,609,143 B2 | 12/2013 | Fischer et al. |
| 8,617,605 B2 | 12/2013 | Fischer et al. |
| 8,623,401 B2 | 1/2014 | Modi |
| 8,623,412 B2 | 1/2014 | Farid et al. |
| 8,652,511 B2 | 2/2014 | Cottrell et al. |
| 8,653,066 B2 | 2/2014 | Bosse |
| 8,658,631 B1 | 2/2014 | Devarakonda et al. |
| 8,685,381 B2 | 4/2014 | Schlessinger et al. |
| 8,709,479 B2 | 4/2014 | Oury et al. |
| 8,722,086 B2 | 5/2014 | Arkenau-Mari et al. |
| 2001/0031278 A1 | 10/2001 | Oshlack et al. |
| 2001/0044472 A1 | 11/2001 | Upadhyay et al. |
| 2001/0046971 A1 | 11/2001 | Hammerly |
| 2002/0055512 A1 | 5/2002 | Marin et al. |
| 2002/0068718 A1 | 6/2002 | Pierce |
| 2002/0099013 A1 | 7/2002 | Piccariello et al. |
| 2002/0164373 A1 | 11/2002 | Maloney |
| 2003/0049318 A1 | 3/2003 | Davis et al. |
| 2003/0068375 A1 | 4/2003 | Wright et al. |
| 2003/0091635 A1 | 5/2003 | Baichwal et al. |
| 2003/0092724 A1 | 5/2003 | Kao et al. |
| 2003/0117622 A1 | 6/2003 | Sevick-Muraca et al. |
| 2003/0125347 A1 | 7/2003 | Anderson et al. |
| 2003/0180362 A1 | 9/2003 | Park et al. |
| 2003/0185761 A1 | 10/2003 | Dugger |
| 2003/0191147 A1 | 10/2003 | Sherman et al. |
| 2003/0199439 A1 | 10/2003 | Simon |
| 2003/0199496 A1 | 10/2003 | Simon |
| 2003/0203027 A1 | 10/2003 | Verreck et al. |
| 2003/0206898 A1 | 11/2003 | Fischkoff et al. |
| 2003/0224051 A1 | 12/2003 | Fink et al. |
| 2003/0235618 A1 | 12/2003 | Moros et al. |
| 2004/0009172 A1 | 1/2004 | Fischkoff et al. |
| 2004/0010000 A1 | 1/2004 | Ayer et al. |
| 2004/0022787 A1 | 2/2004 | Cohen et al. |
| 2004/0029864 A1 | 2/2004 | MacMillan |
| 2004/0043071 A1 | 3/2004 | Pauletti et al. |
| 2004/0062778 A1 | 4/2004 | Shefer et al. |
| 2004/0110781 A1 | 6/2004 | Harmon et al. |
| 2004/0122104 A1 | 6/2004 | Hirsh et al. |
| 2004/0156872 A1 | 8/2004 | Bosch et al. |
| 2004/0157928 A1 | 8/2004 | Kim et al. |
| 2004/0224020 A1 | 11/2004 | Schoenhard |
| 2004/0228802 A1 | 11/2004 | Chang et al. |
| 2004/0250948 A1 | 12/2004 | Tontonoz et al. |
| 2004/0265378 A1 | 12/2004 | Peng et al. |
| 2005/0004098 A1 | 1/2005 | Britten et al. |
| 2005/0013857 A1 | 1/2005 | Fu et al. |
| 2005/0020613 A1 | 1/2005 | Boehm et al. |
| 2005/0026842 A1 | 2/2005 | Simon |
| 2005/0059023 A1 | 3/2005 | Cantor |
| 2005/0106249 A1 | 5/2005 | Hwang et al. |
| 2005/0143471 A1 | 6/2005 | Gao et al. |
| 2005/0152905 A1 | 7/2005 | Omoigui |
| 2005/0169990 A1 | 8/2005 | Kao et al. |
| 2005/0222136 A1 | 10/2005 | Buschmann et al. |
| 2005/0226929 A1 | 10/2005 | Xie et al. |
| 2005/0233459 A1 | 10/2005 | Melker et al. |
| 2005/0245483 A1 | 11/2005 | Brogmann et al. |
| 2005/0265955 A1 | 12/2005 | Raman et al. |
| 2005/0266032 A1 | 12/2005 | Srinivasan et al. |
| 2005/0266072 A1 | 12/2005 | Oshlack et al. |
| 2006/0008527 A1 | 1/2006 | Lagoviyer et al. |
| 2006/0009478 A1 | 1/2006 | Friedmann et al. |
| 2006/0024365 A1 | 2/2006 | Vaya et al. |
| 2006/0039865 A1 | 2/2006 | Preston et al. |
| 2006/0052278 A1 | 3/2006 | Powell |
| 2006/0062734 A1 | 3/2006 | Melker et al. |
| 2006/0067971 A1 | 3/2006 | Story et al. |
| 2006/0073182 A1 | 4/2006 | Wong et al. |
| 2006/0074422 A1 | 4/2006 | Story et al. |
| 2006/0079557 A1 | 4/2006 | Dolle et al. |
| 2006/0093663 A1 | 5/2006 | Suzuki |
| 2006/0099254 A1 | 5/2006 | Desai et al. |
| 2006/0110327 A1 | 5/2006 | Emigh et al. |
| 2006/0111307 A1 | 5/2006 | Robbins |
| 2006/0115527 A1 | 6/2006 | Hassan et al. |
| 2006/0153915 A1 | 7/2006 | Park et al. |
| 2006/0165790 A1 | 7/2006 | Walden et al. |
| 2006/0177380 A1 | 8/2006 | Emigh et al. |
| 2006/0177381 A1 | 8/2006 | Brooks-Korn |
| 2006/0205752 A1 | 9/2006 | Whitehead |
| 2006/0210604 A1 | 9/2006 | Dadey et al. |
| 2006/0210631 A1 | 9/2006 | Patel et al. |
| 2006/0240105 A1 | 10/2006 | Devane et al. |
| 2006/0246134 A1 | 11/2006 | Venkatesh |
| 2006/0263429 A1 | 11/2006 | Feng |
| 2006/0292214 A1 | 12/2006 | Jenkins et al. |
| 2007/0003617 A1 | 1/2007 | Fischer et al. |
| 2007/0003622 A1 | 1/2007 | Srinivasan et al. |
| 2007/0009444 A1 | 1/2007 | Yamaguchi |
| 2007/0020339 A1 | 1/2007 | Bear |
| 2007/0027203 A1 | 2/2007 | Chen et al. |
| 2007/0042969 A1 | 2/2007 | Rauschkolb-Loffler et al. |
| 2007/0048228 A1 | 3/2007 | Arkenau-Maric et al. |
| 2007/0048377 A1 | 3/2007 | Rajabi-Siahboomi et al. |
| 2007/0072982 A1 | 3/2007 | Choi et al. |
| 2007/0087977 A1 | 4/2007 | Robbins |
| 2007/0104788 A1 | 5/2007 | Mulligan |
| 2007/0134493 A1 | 6/2007 | Meghpara |

(56) References Cited

U.S. PATENT DOCUMENTS

| | | |
|---|---|---|
| 2007/0140983 A1 | 6/2007 | Hall et al. |
| 2007/0148239 A1 | 6/2007 | Hall et al. |
| 2007/0167438 A1 | 7/2007 | Rosenzweig-Lipson |
| 2007/0190142 A1 | 8/2007 | Breitenbach et al. |
| 2007/0196491 A1 | 8/2007 | Venkatesh |
| 2007/0197661 A1 | 8/2007 | Bubnis et al. |
| 2007/0207200 A1 | 9/2007 | Plachetka et al. |
| 2007/0207222 A1 | 9/2007 | Yu et al. |
| 2007/0212417 A1 | 9/2007 | Cherukuri |
| 2007/0213717 A1 | 9/2007 | Trieu et al. |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0215511 A1 | 9/2007 | Mehta et al. |
| 2007/0231268 A1 | 10/2007 | Emigh et al. |
| 2007/0232529 A1 | 10/2007 | Mickle et al. |
| 2007/0244093 A1 | 10/2007 | Boehm et al. |
| 2007/0249566 A1 | 10/2007 | Martin et al. |
| 2007/0254027 A1 | 11/2007 | Martin et al. |
| 2007/0281016 A1 | 12/2007 | Kao et al. |
| 2007/0281017 A1 | 12/2007 | Kao et al. |
| 2007/0281018 A1 | 12/2007 | Qiu et al. |
| 2007/0292461 A1 | 12/2007 | Tamarkin et al. |
| 2007/0292508 A1 | 12/2007 | Szamosi et al. |
| 2007/0292510 A1 | 12/2007 | Huang |
| 2007/0298103 A1 | 12/2007 | Hayes |
| 2008/0014228 A1 | 1/2008 | Darmuzey et al. |
| 2008/0014274 A1 | 1/2008 | Bubnis et al. |
| 2008/0020032 A1 | 1/2008 | Crowley et al. |
| 2008/0020039 A1 | 1/2008 | Parikh et al. |
| 2008/0026040 A1 | 1/2008 | Farr et al. |
| 2008/0026062 A1 | 1/2008 | Farr et al. |
| 2008/0031901 A1 | 2/2008 | Qiu et al. |
| 2008/0057122 A1 | 3/2008 | Toney-Parker et al. |
| 2008/0063725 A1 | 3/2008 | Guimberteau et al. |
| 2008/0069871 A1 | 3/2008 | Vaughn et al. |
| 2008/0069878 A1 | 3/2008 | Venkatesh et al. |
| 2008/0069889 A1 | 3/2008 | Cherukuri |
| 2008/0081071 A1 | 4/2008 | Sanghvi et al. |
| 2008/0085304 A1 | 4/2008 | Baichwal et al. |
| 2008/0085312 A1 | 4/2008 | Wilson et al. |
| 2008/0102113 A1 | 5/2008 | Rosenberg |
| 2008/0102123 A1 | 5/2008 | Schachter et al. |
| 2008/0103206 A1 | 5/2008 | Swann et al. |
| 2008/0132751 A1 | 6/2008 | Keller et al. |
| 2008/0152595 A1 | 6/2008 | Emigh et al. |
| 2008/0152704 A1 | 6/2008 | Bonadeo et al. |
| 2008/0171083 A1 | 7/2008 | Staniforth et al. |
| 2008/0175897 A1 | 7/2008 | Plachetka et al. |
| 2008/0193540 A1 | 8/2008 | Soula et al. |
| 2008/0207889 A1 | 8/2008 | Perez et al. |
| 2008/0226702 A1 | 9/2008 | Goldberg |
| 2008/0234237 A1 | 9/2008 | Maddaford et al. |
| 2008/0260815 A1 | 10/2008 | Hayes et al. |
| 2008/0260844 A1 | 10/2008 | Soula et al. |
| 2008/0280837 A1 | 10/2008 | Namburi et al. |
| 2008/0286343 A1 | 11/2008 | Cengic et al. |
| 2008/0286344 A1 | 11/2008 | Darmuzey et al. |
| 2008/0292683 A1 | 11/2008 | Sanghvi et al. |
| 2008/0293695 A1 | 11/2008 | Bristol et al. |
| 2008/0311162 A1 | 12/2008 | Darmuzey et al. |
| 2009/0004267 A1 | 1/2009 | Arkenau-Maric et al. |
| 2009/0004281 A1 | 1/2009 | Nghiem et al. |
| 2009/0004285 A1 | 1/2009 | Yu et al. |
| 2009/0022798 A1 | 1/2009 | Rosenberg et al. |
| 2009/0028873 A1 | 1/2009 | Gant et al. |
| 2009/0035315 A1 | 2/2009 | Christgau et al. |
| 2009/0041838 A1 | 2/2009 | Guimberteau et al. |
| 2009/0061011 A1 | 3/2009 | Talton |
| 2009/0068247 A1 | 3/2009 | Jay |
| 2009/0074866 A1 | 3/2009 | Chen |
| 2009/0081290 A1 | 3/2009 | McKenna et al. |
| 2009/0082466 A1 | 3/2009 | Babul |
| 2009/0087483 A1 | 4/2009 | Sison |
| 2009/0110724 A1 | 4/2009 | Giordano |
| 2009/0124697 A1 | 5/2009 | Cloutier et al. |
| 2009/0143781 A1 | 6/2009 | Cantor et al. |
| 2009/0155193 A1 | 6/2009 | Joabsson et al. |
| 2009/0169626 A1 | 7/2009 | Fleischer et al. |
| 2009/0169631 A1* | 7/2009 | Zamloot .............. A61K 9/14 424/489 |
| 2009/0175939 A1 | 7/2009 | Bosse et al. |
| 2009/0198248 A1 | 8/2009 | Yeung et al. |
| 2009/0220611 A1 | 9/2009 | Dargelas et al. |
| 2009/0220613 A1 | 9/2009 | Odidi et al. |
| 2009/0232887 A1 | 9/2009 | Odidi et al. |
| 2009/0238873 A1 | 9/2009 | Chattaraj et al. |
| 2009/0246257 A1 | 10/2009 | Modi |
| 2009/0258947 A1 | 10/2009 | Jain et al. |
| 2009/0317355 A1 | 12/2009 | Roth et al. |
| 2010/0003322 A1 | 1/2010 | Lai et al. |
| 2010/0003332 A1 | 1/2010 | Bae et al. |
| 2010/0010030 A1 | 1/2010 | Jain et al. |
| 2010/0021543 A1 | 1/2010 | Schierstedt |
| 2010/0041759 A1 | 2/2010 | Wilson et al. |
| 2010/0048602 A1 | 2/2010 | Riggs-Sauthier et al. |
| 2010/0051801 A1 | 3/2010 | Erfurth et al. |
| 2010/0076074 A1 | 3/2010 | Gant et al. |
| 2010/0080829 A1 | 4/2010 | Dulieu et al. |
| 2010/0098746 A1 | 4/2010 | King |
| 2010/0099696 A1 | 4/2010 | Soscia et al. |
| 2010/0111830 A1 | 5/2010 | Boyden et al. |
| 2010/0143449 A1 | 6/2010 | Kolesnikov |
| 2010/0152299 A1 | 6/2010 | Vasanthavada et al. |
| 2010/0172989 A1 | 7/2010 | Roth et al. |
| 2010/0196471 A1 | 8/2010 | Jain et al. |
| 2010/0196474 A1 | 8/2010 | Han et al. |
| 2010/0204259 A1 | 8/2010 | Tygesen et al. |
| 2010/0215737 A1 | 8/2010 | Coulter |
| 2010/0226943 A1 | 9/2010 | Brennan et al. |
| 2010/0226978 A1 | 9/2010 | Petereit et al. |
| 2010/0239667 A1 | 9/2010 | Hemmingsen et al. |
| 2010/0249045 A1 | 9/2010 | Babul |
| 2010/0260858 A1 | 10/2010 | Ruddy et al. |
| 2010/0266682 A1 | 10/2010 | Davar et al. |
| 2010/0281205 A1 | 11/2010 | Downie et al. |
| 2010/0286100 A1 | 11/2010 | First et al. |
| 2010/0291201 A1 | 11/2010 | Shah et al. |
| 2010/0304998 A1 | 12/2010 | Sem |
| 2011/0003005 A1 | 1/2011 | Venkatesh et al. |
| 2011/0003006 A1 | 1/2011 | Venkatesh et al. |
| 2011/0008424 A1 | 1/2011 | Chang et al. |
| 2011/0020440 A1 | 1/2011 | Modi et al. |
| 2011/0020451 A1 | 1/2011 | Bartholomaus et al. |
| 2011/0020776 A1 | 1/2011 | Nielsen et al. |
| 2011/0038930 A1 | 2/2011 | Barnscheid et al. |
| 2011/0052685 A1 | 3/2011 | Hou et al. |
| 2011/0077238 A1 | 3/2011 | Leech et al. |
| 2011/0091537 A1 | 4/2011 | Castan et al. |
| 2011/0091563 A1 | 4/2011 | Kurasawa et al. |
| 2011/0104214 A1 | 5/2011 | Oshlack et al. |
| 2011/0104272 A1 | 5/2011 | Hou |
| 2011/0118189 A1 | 5/2011 | Farr et al. |
| 2011/0129530 A1 | 6/2011 | Venkatesh et al. |
| 2011/0142905 A1 | 6/2011 | Bar-Shalom et al. |
| 2011/0142943 A1 | 6/2011 | Rariy et al. |
| 2011/0150989 A1 | 6/2011 | Park et al. |
| 2011/0159048 A1 | 6/2011 | Crain et al. |
| 2011/0159100 A1 | 6/2011 | Andersen et al. |
| 2011/0160239 A1 | 6/2011 | Brodbeck et al. |
| 2011/0165248 A1 | 7/2011 | Machonis |
| 2011/0182987 A1 | 7/2011 | Bawa et al. |
| 2011/0195116 A1 | 8/2011 | Hobbs et al. |
| 2011/0195520 A1 | 8/2011 | Leider et al. |
| 2011/0195989 A1 | 8/2011 | Rudnic et al. |
| 2011/0207761 A1 | 8/2011 | Losev et al. |
| 2011/0218209 A1 | 9/2011 | Yered |
| 2011/0229562 A1 | 9/2011 | Bar et al. |
| 2011/0230816 A1 | 9/2011 | Copp-Howland |
| 2011/0237614 A1 | 9/2011 | Jude-Fishburn et al. |
| 2011/0239745 A1 | 10/2011 | Satcher, Jr. et al. |
| 2011/0245208 A1 | 10/2011 | Diatchenko et al. |
| 2011/0262539 A1 | 10/2011 | Bosse et al. |

(56) References Cited

U.S. PATENT DOCUMENTS

| | | |
|---|---|---|
| 2011/0287095 A1 | 11/2011 | Park et al. |
| 2011/0311626 A1 | 12/2011 | Venkatesh et al. |
| 2011/0311628 A1 | 12/2011 | Muthusamy et al. |
| 2011/0311631 A1 | 12/2011 | Baer et al. |
| 2012/0009129 A1 | 1/2012 | Brzeczko |
| 2012/0010157 A1 | 1/2012 | Polvino et al. |
| 2012/0015007 A1 | 1/2012 | Bredenberg et al. |
| 2012/0015031 A1 | 1/2012 | Sesha |
| 2012/0021370 A1 | 1/2012 | Drapeau et al. |
| 2012/0022009 A1 | 1/2012 | Bryant |
| 2012/0034306 A1 | 2/2012 | Pollock et al. |
| 2012/0039957 A1 | 2/2012 | Brzeczko et al. |
| 2012/0045506 A1 | 2/2012 | Baer et al. |
| 2012/0059065 A1 | 3/2012 | Barnscheid et al. |
| 2012/0063996 A1 | 3/2012 | Bosch et al. |
| 2012/0064159 A1 | 3/2012 | Chauhan et al. |
| 2012/0065220 A1 | 3/2012 | Barnscheid et al. |
| 2012/0083506 A1 | 4/2012 | Herry et al. |
| 2012/0088786 A1 | 4/2012 | Dadagher et al. |
| 2012/0093929 A1 | 4/2012 | Oksche et al. |
| 2012/0100183 A1 | 4/2012 | Schlessinger et al. |
| 2012/0107400 A1 | 5/2012 | Muthusamy et al. |
| 2012/0121594 A1 | 5/2012 | Smith |
| 2012/0121724 A1 | 5/2012 | Maibach |
| 2012/0135075 A1 | 5/2012 | Mohammad |
| 2012/0135077 A1 | 5/2012 | Mehta et al. |
| 2012/0141554 A1 | 6/2012 | Dill |
| 2012/0164209 A1 | 6/2012 | Shah et al. |
| 2012/0164220 A1 | 6/2012 | Huang |
| 2012/0202838 A1 | 8/2012 | Ghosh et al. |
| 2012/0205532 A1 | 8/2012 | Mazza |
| 2012/0207825 A1 | 8/2012 | Roy et al. |
| 2012/0237556 A1 | 9/2012 | Schlessinger et al. |
| 2012/0245156 A1 | 9/2012 | Nguyen |
| 2012/0251590 A1 | 10/2012 | Cruz et al. |
| 2012/0282335 A1 | 11/2012 | Venkatesh et al. |
| 2012/0289534 A1 | 11/2012 | Pergolizzi et al. |
| 2012/0321674 A1 | 12/2012 | Vachon et al. |
| 2013/0004415 A1 | 1/2013 | Moudgil et al. |
| 2013/0011479 A1 | 1/2013 | Angeli et al. |
| 2013/0017262 A1 | 1/2013 | Mullen et al. |
| 2013/0022646 A1 | 1/2013 | Rudnic et al. |
| 2013/0022676 A1 | 1/2013 | Mullen et al. |
| 2013/0022677 A1 | 1/2013 | Mullen et al. |
| 2013/0023553 A1 | 1/2013 | Jude-Fishburn et al. |
| 2013/0028955 A1 | 1/2013 | Tolia |
| 2013/0028970 A1 | 1/2013 | Schwier et al. |
| 2013/0028972 A1 | 1/2013 | Schwier et al. |
| 2013/0030360 A1 | 1/2013 | Stopek et al. |
| 2013/0059010 A1 | 3/2013 | Herry et al. |
| 2013/0102959 A1 | 4/2013 | Stopek et al. |
| 2013/0115249 A1 | 5/2013 | Vergez et al. |
| 2013/0122098 A1 | 5/2013 | First et al. |
| 2013/0122101 A1 | 5/2013 | Habib et al. |
| 2013/0123294 A1 | 5/2013 | Lebon et al. |
| 2013/0129825 A1 | 5/2013 | Billoet |
| 2013/0129826 A1 | 5/2013 | Gei Ler et al. |
| 2013/0129828 A1 | 5/2013 | Talton |
| 2013/0136792 A1 | 5/2013 | Draper et al. |
| 2013/0156853 A1 | 6/2013 | Zhang et al. |
| 2013/0165467 A1 | 6/2013 | Hayes et al. |
| 2013/0168321 A1 | 7/2013 | Cannon et al. |
| 2013/0197021 A1 | 8/2013 | Mohammad et al. |
| 2013/0209557 A1 | 8/2013 | Barnscheid |
| 2013/0209561 A1 | 8/2013 | Kao et al. |
| 2013/0217777 A1 | 8/2013 | Kirkorian |
| 2013/0225412 A1 | 8/2013 | Sardari Lodriche et al. |
| 2013/0225625 A1 | 8/2013 | Barnscheid et al. |
| 2013/0225697 A1 | 8/2013 | Barnscheid et al. |
| 2013/0230587 A1 | 9/2013 | Pilgaonkar et al. |
| 2013/0237559 A1 | 9/2013 | Ortiz et al. |
| 2013/0245054 A1 | 9/2013 | Prater et al. |
| 2013/0259941 A1 | 10/2013 | O'Donnell |
| 2013/0273153 A1 | 10/2013 | Park et al. |
| 2013/0273162 A1 | 10/2013 | Li |
| 2013/0280176 A1 | 10/2013 | Diezi et al. |
| 2013/0280177 A1 | 10/2013 | Raman et al. |
| 2013/0280338 A1 | 10/2013 | Wening et al. |
| 2013/0303623 A1 | 11/2013 | Barnscheid et al. |
| 2013/0330409 A1 | 12/2013 | Mohammad |
| 2013/0345250 A1 | 12/2013 | Fleming |
| 2014/0010873 A1 | 1/2014 | Tygesen et al. |
| 2014/0010874 A1 | 1/2014 | Sackler |
| 2014/0017310 A1 | 1/2014 | Gower et al. |
| 2014/0031734 A1 | 1/2014 | Saxena et al. |
| 2014/0045801 A1 | 2/2014 | Rossi |
| 2014/0050787 A1 | 2/2014 | Tygesen et al. |
| 2014/0056979 A1 | 2/2014 | Huang |
| 2014/0066516 A1 | 3/2014 | Clarke et al. |
| 2014/0094438 A1 | 4/2014 | Mitchell |
| 2014/0105967 A1 | 4/2014 | Rariy et al. |
| 2014/0105977 A1 | 4/2014 | Devarakonda et al. |
| 2014/0112984 A1 | 4/2014 | Arkenau-Maric et al. |
| 2014/0112989 A1 | 4/2014 | Bartholomaus et al. |
| 2014/0127300 A1 | 5/2014 | Tengler et al. |
| 2014/0171481 A1 | 6/2014 | Liepold et al. |
| 2015/0057304 A1 | 2/2015 | Thompson et al. |
| 2015/0111862 A1* | 4/2015 | Podolski ............... A61K 9/0034 514/179 |
| 2015/0283087 A1 | 10/2015 | Vamvakas et al. |

FOREIGN PATENT DOCUMENTS

| | | |
|---|---|---|
| CA | 285559 A | 11/1926 |
| CA | 2319353 A1 | 8/1999 |
| CA | 2408106 A1 | 11/2001 |
| CA | 2386794 A1 | 1/2002 |
| CA | 2544404 A1 | 6/2005 |
| CA | 2573583 A1 | 2/2006 |
| CA | 2649265 A1 | 8/2007 |
| CA | 2690829 A1 | 1/2009 |
| CA | 2737307 A1 | 4/2010 |
| CA | 2750400 A1 | 7/2010 |
| CA | 2766179 A1 | 12/2010 |
| CA | 2847613 A1 | 3/2013 |
| CN | 101824144 A | 9/2010 |
| CN | 101987081 A | 3/2011 |
| CN | 102344534 A | 2/2012 |
| CN | 102389423 A | 3/2012 |
| CN | 102648985 A | 8/2012 |
| CN | 103040829 A | 4/2013 |
| CN | 103070840 A | 5/2013 |
| CN | 103637987 A | 3/2014 |
| CN | 103637998 A | 3/2014 |
| DE | 2326141 A1 | 12/1973 |
| DE | 2705051 A1 | 8/1977 |
| DE | 10215067 A1 | 10/2003 |
| DE | 10215131 A1 | 10/2003 |
| DE | 202006014131 U1 | 1/2007 |
| DE | 102007021549 A1 | 11/2008 |
| EP | 103991 A2 | 3/1984 |
| EP | 0152292 A2 | 8/1985 |
| EP | 459387 A2 | 12/1991 |
| EP | 0960620 A1 | 12/1999 |
| EP | 1663229 A2 | 6/2006 |
| EP | 1980245 A1 | 10/2008 |
| EP | 2007360 A1 | 12/2008 |
| EP | 2067471 A1 | 6/2009 |
| EP | 2106799 A1 | 10/2009 |
| EP | 2123626 A1 | 11/2009 |
| EP | 2343071 A1 | 7/2011 |
| EP | 2359812 A1 | 8/2011 |
| EP | 2444064 A1 | 4/2012 |
| EP | 2457900 A1 | 5/2012 |
| EP | 2548863 A1 | 1/2013 |
| EP | 2548876 A1 | 1/2013 |
| EP | 2586607 A1 | 5/2013 |
| EP | 2626358 A1 | 8/2013 |
| FR | 2850576 A1 | 8/2004 |
| FR | 2878158 A1 | 5/2006 |
| FR | 2878161 A1 | 5/2006 |
| FR | 2892937 A1 | 5/2007 |
| FR | 2960775 A1 | 12/2011 |
| GB | 135381 A | 12/1919 |

(56) References Cited

FOREIGN PATENT DOCUMENTS

| | | |
|---|---|---|
| HU | 9903375 A2 | 2/2000 |
| IN | 2005MU01013 | 6/2007 |
| IN | 2006KO00351 | 7/2007 |
| IN | 2005MU01012 | 8/2007 |
| IN | 2009DE00453 | 4/2013 |
| JP | 55084166 | 12/1978 |
| JP | 60092214 | 5/1985 |
| JP | 11033084 | 2/1999 |
| JP | 2007-523872 A | 8/2007 |
| JP | 2008-523798 A | 7/2008 |
| JP | 2009256214 A | 11/2009 |
| JP | 2010053078 A | 3/2010 |
| JP | 2010173976 A | 8/2010 |
| JP | 2011256115 A | 12/2011 |
| JP | 2013-523873 A | 6/2013 |
| JP | 2013249458 A | 12/2013 |
| KR | 2008026754 | 3/2008 |
| KR | 1203186 | 11/2012 |
| PL | 133984 B2 | 7/1985 |
| WO | WO-8503439 A1 | 8/1985 |
| WO | WO-9107950 A1 | 6/1991 |
| WO | WO-9324154 A1 | 12/1993 |
| WO | WO-9408551 A2 | 4/1994 |
| WO | WO-9418970 A1 | 9/1994 |
| WO | WO-9425009 A1 | 11/1994 |
| WO | WO-9426731 A1 | 11/1994 |
| WO | WO-9523591 A1 | 9/1995 |
| WO | WO-9614059 A1 | 5/1996 |
| WO | WO-9623486 A1 | 8/1996 |
| WO | WO-9704780 A2 | 2/1997 |
| WO | WO-9720556 A1 | 6/1997 |
| WO | WO-9720561 A1 | 6/1997 |
| WO | WO-97/33566 A2 | 9/1997 |
| WO | WO-9803179 A1 | 1/1998 |
| WO | WO-9818610 A1 | 5/1998 |
| WO | WO-98/25613 A2 | 6/1998 |
| WO | WO-9332427 A1 | 7/1998 |
| WO | WO-9650044 A1 | 11/1998 |
| WO | WO-9650075 A1 | 11/1998 |
| WO | WO-9907413 A1 | 2/1999 |
| WO | WO-9944591 A1 | 9/1999 |
| WO | WO-9953922 A1 | 10/1999 |
| WO | WO-9966919 A1 | 12/1999 |
| WO | WO-2000021504 A1 | 4/2000 |
| WO | WO-2000029022 A1 | 5/2000 |
| WO | WO-2000029023 A1 | 5/2000 |
| WO | WO-2000038649 A1 | 7/2000 |
| WO | WO-2000061537 A2 | 10/2000 |
| WO | WO-2000061541 A2 | 10/2000 |
| WO | WO-2001008662 A1 | 2/2001 |
| WO | WO-2001012584 A2 | 2/2001 |
| WO | WO-2001015667 A1 | 3/2001 |
| WO | WO-2001032101 A1 | 5/2001 |
| WO | WO-2001032928 A2 | 5/2001 |
| WO | WO-2001076576 A2 | 10/2001 |
| WO | WO-2001085150 A2 | 11/2001 |
| WO | WO-2001085257 A2 | 11/2001 |
| WO | WO-2001091736 A2 | 12/2001 |
| WO | WO-2002005647 A1 | 1/2002 |
| WO | WO 2002032395 A2 | 4/2002 |
| WO | WO-2002034237 A1 | 5/2002 |
| WO | WO-2002051432 A1 | 7/2002 |
| WO | WO-2002056861 A2 | 7/2002 |
| WO | WO-2002100351 A2 | 12/2002 |
| WO | WO-2003004009 A1 | 1/2003 |
| WO | WO-2003013481 A1 | 2/2003 |
| WO | WO-2003020200 A2 | 3/2003 |
| WO | WO-2003024430 A1 | 3/2003 |
| WO | WO-2003032990 A2 | 4/2003 |
| WO | WO-2003034991 A2 | 5/2003 |
| WO | WO-2003051878 A2 | 6/2003 |
| WO | WO-2003063834 A1 | 8/2003 |
| WO | WO-2003065988 A2 | 8/2003 |
| WO | WO-2003066029 A2 | 8/2003 |
| WO | WO-2003066030 A2 | 8/2003 |
| WO | WO-2003068197 A1 | 8/2003 |
| WO | WO-2003079972 A2 | 10/2003 |
| WO | WO-2003088991 A1 | 10/2003 |
| WO | WO-2003092648 A1 | 11/2003 |
| WO | WO-2003101476 A1 | 12/2003 |
| WO | WO-2004026256 A2 | 4/2004 |
| WO | WO-2004039320 A1 | 5/2004 |
| WO | WO-2004045551 A2 | 6/2004 |
| WO | WO-2004054542 A2 | 7/2004 |
| WO | WO-2004064832 A2 | 8/2004 |
| WO | WO-2004069135 A2 | 8/2004 |
| WO | WO-2004075832 A2 | 9/2004 |
| WO | WO-2004082588 A2 | 9/2004 |
| WO | WO-2004082719 A1 | 9/2004 |
| WO | WO-2004084868 A1 | 10/2004 |
| WO | WO-2004108163 A1 | 12/2004 |
| WO | WO-2005000310 A1 | 1/2005 |
| WO | WO-2005000331 A2 | 1/2005 |
| WO | WO-2005002597 A1 | 1/2005 |
| WO | WO-2005004989 A2 | 1/2005 |
| WO | 2005/009409 A2 | 2/2005 |
| WO | WO-2005009409 A2 | 2/2005 |
| WO | WO-2005028539 A2 | 3/2005 |
| WO | WO-2005030181 A1 | 4/2005 |
| WO | WO-2005030182 A1 | 4/2005 |
| WO | WO-2005032474 A2 | 4/2005 |
| WO | WO-2005032555 A2 | 4/2005 |
| WO | WO-2005038049 A2 | 4/2005 |
| WO | WO-2005046727 A2 | 5/2005 |
| WO | WO-2005051356 A1 | 6/2005 |
| WO | WO-2005058303 A1 | 6/2005 |
| WO | WO-2005063206 A1 | 7/2005 |
| WO | WO-2005063219 A2 | 7/2005 |
| WO | WO-2005070465 A2 | 8/2005 |
| WO | WO-2005079760 A1 | 9/2005 |
| WO | WO-2005092306 A1 | 10/2005 |
| WO | WO-2005102338 A1 | 11/2005 |
| WO | WO-2005103070 A1 | 11/2005 |
| WO | WO-2005107467 A2 | 11/2005 |
| WO | WO-2005107726 A2 | 11/2005 |
| WO | WO-2005123192 A2 | 12/2005 |
| WO | WO-2005123193 A2 | 12/2005 |
| WO | WO-2006014967 A1 | 2/2006 |
| WO | WO-2006020930 A2 | 2/2006 |
| WO | WO-2006024018 A2 | 3/2006 |
| WO | WO-2006024881 A2 | 3/2006 |
| WO | WO-2006030402 A2 | 3/2006 |
| WO | WO-2006046114 A2 | 5/2006 |
| WO | WO-2006050165 A2 | 5/2006 |
| WO | 2006/064235 A2 | 6/2006 |
| WO | WO-2006069030 A1 | 6/2006 |
| WO | WO-2006069202 A2 | 6/2006 |
| WO | WO-2006075123 A1 | 7/2006 |
| WO | WO-2006085101 A2 | 8/2006 |
| WO | WO-2006092691 A1 | 9/2006 |
| WO | WO-2006099541 A2 | 9/2006 |
| WO | WO-2006103418 A1 | 10/2006 |
| WO | WO-2006103551 A1 | 10/2006 |
| WO | WO-2006105205 A1 | 10/2006 |
| WO | WO-2006116148 A2 | 11/2006 |
| WO | WO-2006133733 A1 | 12/2006 |
| WO | WO-2006138278 A1 | 12/2006 |
| WO | WO-2007021970 A2 | 2/2007 |
| WO | WO-2007036671 A2 | 4/2007 |
| WO | WO-2007050631 A2 | 5/2007 |
| WO | WO-2007056142 A2 | 5/2007 |
| WO | WO-2007058960 A1 | 5/2007 |
| WO | WO-2007/070632 A2 | 6/2007 |
| WO | WO-2007072503 A2 | 6/2007 |
| WO | WO-2007087452 A2 | 8/2007 |
| WO | WO-2007089328 A2 | 8/2007 |
| WO | WO-2007094694 A1 | 8/2007 |
| WO | WO-2007106550 A2 | 9/2007 |
| WO | WO-2007128349 A1 | 11/2007 |
| WO | WO-2007128884 A1 | 11/2007 |
| WO | WO-2007131357 A1 | 11/2007 |
| WO | WO-2007133583 A2 | 11/2007 |
| WO | WO-2007135193 A2 | 11/2007 |
| WO | WO-2007141328 A1 | 12/2007 |

(56) References Cited

FOREIGN PATENT DOCUMENTS

| | | |
|---|---|---|
| WO | WO-2007149438 A2 | 12/2007 |
| WO | WO-2008001341 A1 | 1/2008 |
| WO | WO-2008007152 A2 | 1/2008 |
| WO | WO-2008008364 A2 | 1/2008 |
| WO | WO-2008011169 A2 | 1/2008 |
| WO | WO-2008013710 A2 | 1/2008 |
| WO | WO-2008/021394 A2 | 2/2008 |
| WO | WO-2008023261 A1 | 2/2008 |
| WO | WO-2008027350 A2 | 3/2008 |
| WO | WO-2008027442 A2 | 3/2008 |
| WO | WO-2008033351 A2 | 3/2008 |
| WO | WO-2008033523 A1 | 3/2008 |
| WO | WO-2008057579 A2 | 5/2008 |
| WO | WO-2008057608 A2 | 5/2008 |
| WO | WO-2008060552 A2 | 5/2008 |
| WO | WO-2008063625 A2 | 5/2008 |
| WO | WO-2008067222 A1 | 6/2008 |
| WO | WO-2008068471 A1 | 6/2008 |
| WO | WO-2008070268 A2 | 6/2008 |
| WO | WO-2008086804 A2 | 7/2008 |
| WO | WO-2008097976 A1 | 8/2008 |
| WO | WO-2008100977 A2 | 8/2008 |
| WO | WO-2008106429 A2 | 9/2008 |
| WO | WO-2008107410 A1 | 9/2008 |
| WO | WO-2008108957 A2 | 9/2008 |
| WO | WO-2008108958 A2 | 9/2008 |
| WO | WO-2008108986 A2 | 9/2008 |
| WO | WO-2008131056 A2 | 10/2008 |
| WO | WO-2008131057 A2 | 10/2008 |
| WO | WO-2008132712 A2 | 11/2008 |
| WO | WO-2008133928 A2 | 11/2008 |
| WO | WO-2008134600 A1 | 11/2008 |
| WO | WO-2008135283 A1 | 11/2008 |
| WO | WO-2008140459 A1 | 11/2008 |
| WO | WO-2008140460 A1 | 11/2008 |
| WO | WO-2008140461 A1 | 11/2008 |
| WO | WO-2008141189 A1 | 11/2008 |
| WO | WO-2008148798 A2 | 12/2008 |
| WO | WO-2008155620 A1 | 12/2008 |
| WO | WO-2008157308 A2 | 12/2008 |
| WO | WO-2009002299 A1 | 12/2008 |
| WO | WO-2009005613 A2 | 1/2009 |
| WO | WO-2009005803 A1 | 1/2009 |
| WO | WO-2009014534 A1 | 1/2009 |
| WO | WO-2009021055 A1 | 2/2009 |
| WO | WO-2009023672 A2 | 2/2009 |
| WO | WO-2009026241 A1 | 2/2009 |
| WO | WO-2009042960 A1 | 4/2009 |
| WO | WO-2009047175 A2 | 4/2009 |
| WO | WO-2009073686 A1 | 6/2009 |
| WO | WO-2009076361 A1 | 6/2009 |
| WO | WO-2009076764 A1 | 6/2009 |
| WO | WO-2009089134 A1 | 7/2009 |
| WO | WO-2009100118 A1 | 8/2009 |
| WO | WO-2009104838 A1 | 8/2009 |
| WO | WO-2009109911 A1 | 9/2009 |
| WO | WO-2009114648 A1 | 9/2009 |
| WO | WO-2009118764 A1 | 10/2009 |
| WO | WO-2009120889 A2 | 10/2009 |
| WO | WO-2009121496 A2 | 10/2009 |
| WO | WO-2009124755 A1 | 10/2009 |
| WO | WO-2009126931 A2 | 10/2009 |
| WO | WO-2009/137086 A1 | 11/2009 |
| WO | WO-2009134336 A1 | 11/2009 |
| WO | WO-2009143295 A1 | 11/2009 |
| WO | WO-2009143299 A1 | 11/2009 |
| WO | WO-2009/152133 A1 | 12/2009 |
| WO | WO-2010000073 A1 | 1/2010 |
| WO | WO-2010017821 A1 | 2/2010 |
| WO | WO-2010032128 A1 | 3/2010 |
| WO | WO-2010033195 A1 | 3/2010 |
| WO | WO-2010068789 A1 | 6/2010 |
| WO | WO-2010069050 A1 | 6/2010 |
| WO | WO-2010083894 A1 | 7/2010 |
| WO | WO-2010089132 A1 | 8/2010 |
| WO | WO-2010096045 A1 | 8/2010 |
| WO | WO-2010103365 A2 | 9/2010 |
| WO | WO-2010103367 A1 | 9/2010 |
| WO | WO-2010123999 A2 | 10/2010 |
| WO | WO-2010124089 A2 | 10/2010 |
| WO | WO-2010127345 A2 | 11/2010 |
| WO | WO-2010127346 A2 | 11/2010 |
| WO | WO-2010132095 A1 | 11/2010 |
| WO | WO-2010135340 A2 | 11/2010 |
| WO | WO-2010140007 A2 | 12/2010 |
| WO | WO-2010141505 A1 | 12/2010 |
| WO | WO-2010150930 A1 | 12/2010 |
| WO | WO-2010151020 A2 | 12/2010 |
| WO | WO-2010151823 A1 | 12/2010 |
| WO | WO-2011005671 A1 | 1/2011 |
| WO | WO-2011006012 A1 | 1/2011 |
| WO | WO-2011008298 A2 | 1/2011 |
| WO | WO-2011009603 A1 | 1/2011 |
| WO | WO-2011009604 A1 | 1/2011 |
| WO | WO-2011011060 A1 | 1/2011 |
| WO | WO-2011011199 A1 | 1/2011 |
| WO | WO-2011011543 A1 | 1/2011 |
| WO | WO-2011012715 A1 | 2/2011 |
| WO | WO-2011039768 A2 | 4/2011 |
| WO | WO-2011045769 A2 | 4/2011 |
| WO | WO-2011057199 A1 | 5/2011 |
| WO | WO-2011066287 A1 | 6/2011 |
| WO | WO-2011066980 A2 | 6/2011 |
| WO | WO-2011068723 A1 | 6/2011 |
| WO | WO-2011068881 A1 | 6/2011 |
| WO | WO-2011084593 A2 | 7/2011 |
| WO | WO-2011086193 A1 | 7/2011 |
| WO | WO-2011088140 A1 | 7/2011 |
| WO | WO-2011106076 A2 | 9/2011 |
| WO | WO-2011107750 A2 | 9/2011 |
| WO | WO-2011107855 A2 | 9/2011 |
| WO | 2011/128635 A2 | 10/2011 |
| WO | WO-2011120084 A1 | 10/2011 |
| WO | WO-2011123719 A2 | 10/2011 |
| WO | WO-2011123866 A1 | 10/2011 |
| WO | WO-2011127467 A1 | 10/2011 |
| WO | WO-2011139595 A2 | 11/2011 |
| WO | WO-2012007159 A2 | 1/2012 |
| WO | WO-2012011917 A1 | 1/2012 |
| WO | WO-2012016569 A1 | 2/2012 |
| WO | WO-2012020097 A2 | 2/2012 |
| WO | WO-2012021819 A1 | 2/2012 |
| WO | WO-2012026319 A1 | 3/2012 |
| WO | WO-2012037457 A1 | 3/2012 |
| WO | WO-2012052955 A1 | 4/2012 |
| WO | WO-2012054071 A1 | 4/2012 |
| WO | WO-2012054831 A2 | 4/2012 |
| WO | WO-2012061779 A1 | 5/2012 |
| WO | WO-2012063257 A2 | 5/2012 |
| WO | WO-2012069175 A1 | 5/2012 |
| WO | WO-2012076907 A2 | 6/2012 |
| WO | WO-2012077110 A2 | 6/2012 |
| WO | WO-2012085236 A1 | 6/2012 |
| WO | WO-2012085656 A2 | 6/2012 |
| WO | WO-2012085657 A2 | 6/2012 |
| WO | WO-2012087377 A1 | 6/2012 |
| WO | WO-2012098281 A2 | 7/2012 |
| WO | WO-2012106343 A2 | 8/2012 |
| WO | WO-2012112933 A1 | 8/2012 |
| WO | WO-2012112952 A1 | 8/2012 |
| WO | WO-2012116278 A1 | 8/2012 |
| WO | WO-2012116279 A1 | 8/2012 |
| WO | WO-2012121461 A1 | 9/2012 |
| WO | WO-2012127506 A1 | 9/2012 |
| WO | WO-2012131463 A2 | 10/2012 |
| WO | WO-2012139191 A1 | 10/2012 |
| WO | WO-2012177986 A2 | 12/2012 |
| WO | WO-2013000578 A1 | 1/2013 |
| WO | WO-2013003845 A1 | 1/2013 |
| WO | WO-2013010880 A1 | 1/2013 |
| WO | WO-2013010881 A1 | 1/2013 |
| WO | WO-2013015545 A1 | 1/2013 |
| WO | WO-2013038267 A1 | 3/2013 |
| WO | WO-2013038268 A1 | 3/2013 |

(56) References Cited

FOREIGN PATENT DOCUMENTS

| WO | WO-2013050539 A2 | 4/2013 |
|---|---|---|
| WO | WO-2013057570 A2 | 4/2013 |
| WO | WO-2013058496 A1 | 4/2013 |
| WO | WO-2013059805 A1 | 4/2013 |
| WO | WO-2013061161 A2 | 5/2013 |
| WO | WO-2013070617 A1 | 5/2013 |
| WO | WO-2013072395 A1 | 5/2013 |
| WO | WO-2015077851 A1 | 5/2013 |
| WO | WO-2013082308 A1 | 6/2013 |
| WO | WO-2013083710 A1 | 6/2013 |
| WO | WO-2013084059 A1 | 6/2013 |
| WO | WO-2013093877 A2 | 6/2013 |
| WO | WO-2013103537 A1 | 7/2013 |
| WO | WO-2013119231 A1 | 8/2013 |
| WO | WO-2013128276 A2 | 9/2013 |
| WO | WO-2013128447 A1 | 9/2013 |
| WO | WO-2013136078 A1 | 9/2013 |
| WO | WO-2013138118 A1 | 9/2013 |
| WO | WO-2013151638 A1 | 10/2013 |
| WO | WO-2013155430 A1 | 10/2013 |
| WO | WO-2013158810 A1 | 10/2013 |
| WO | WO-2013158814 A1 | 10/2013 |
| WO | WO-2013170052 A1 | 11/2013 |
| WO | WO-2013171146 A1 | 11/2013 |
| WO | WO-2013175511 A1 | 11/2013 |
| WO | WO-2014001268 A1 | 1/2014 |
| WO | WO-2014001904 A1 | 1/2014 |
| WO | WO-2014001905 A1 | 1/2014 |
| WO | WO-2014011830 A1 | 1/2014 |
| WO | WO-2014036004 A1 | 1/2014 |
| WO | WO-2014025638 A1 | 2/2014 |
| WO | WO-2014045605 A1 | 3/2014 |
| WO | WO-2014047731 A1 | 4/2014 |
| WO | WO-2014059512 A1 | 4/2014 |
| WO | WO-2015023675 A2 | 2/2015 |
| WO | WO-2015023704 A1 | 2/2015 |
| WO | 2016/010771 A1 | 1/2016 |

OTHER PUBLICATIONS

Sako et al., "Relationship between gelation rate of controlled-release acetaminophen tablets containing polyethylene bride and colonic drug release in dogs", Pharmaceutical Research, 1996, vol. 13, No. 4, pp. 594-596.

Djuris et al., "Application of quality by design concepts in the development of fluidized bed granulation and tableting processes", Journal of Pharmaceutical Sciences, 2013, vol. 102, No. 6, pp. 1869-1882.

Dahl et al., "Mechanisms to control drug release from pellets coated with a silicone elastomer aqueous dispersion", Pharmaceutical Research, 1992. vol. 9, No. 3, pp. 398-405.

Sako, et al., "Influence of water soluble fillers in hydroxypropylmethylcellulose matrices on in vitro and in vivo drug release", Journal of Controlled Release, 2002, vol. 81, No. 1-2, pp. 165-172.

Borini et al., "Hot melt granulation of coarse pharmaceutical powders in a spouted bed", Powder Technology, 2009, vol. 189, No. 3, pp. 520-527.

Gohel et al., "Fabrication and Evaluation of Bi-layer Tablet Containing Conventional Paracetamol and Modified Release Diclofenac Sodium", Indian J. Pharm Sci., 2010, vol. 72, No. 2. pp. 191-196.

Stambaugh et al., "Double-blind, randomized comparison of the analgesic and pharmacokinetic profiles of controlled- and immediate-release oral oxycodone in cancer pain patients", 2001, vol. 41, No. 5, pp. 500-506.

Sunshine et al., "Analgesic Efficacy of Controlled-Release Oxycodone in Postoperative Pain", Journal of Clinical Pharmacology, 1996, vol. 36, No. 7, pp. 595-603.

Harris, et al., "Abuse potential, pharmacokinetics, pharmacodynamics, and safety of intranasally administered crushed oxycodone HCI abuse-deterrent controlled-release tablets in recreational opioid users", Journal of Clinical Pharmacology, 2014, vol. 54, No. 4, pp. 468-477.

Gosai et al., "Bioequivalence of oxycodone hydrochoride extended release tablets to marketed reference products OxyContin® in Canada and US", Int J Clin Pharmacol Ther., 2013, vol. 51, No. 11, pp. 895-907.

Upadhye et al., "Polyethylene Oxide and Ethylcellulose for Tamper Resistance and Controlled Drug Delivery", Melt Extrusion, AAPS Advances in the Pharmaceutical Sciences Series, 2013, vol. 9, pp. 145-158.

Benziger et al., "Differential Effects of Food on the Bioavailability of Controlled-Release Oxycodone Tablets and Immediate-Release Oxycodone Solution", Journal of Pharmaceutical Sciences, vol. 85, No. 4, pp. 407-410.

International Search Report for International Application No. PCT/US14/50737; International Filing Date Aug. 12, 2014.

Bartholomaus et al., "New Abuse Deterrent Formulation (ADF) Technology for Immediate-Release Opioids". Drug Development & Delivery, 2013, vol. 13, No. 8, pp. 76-81.

Third Party Observation dated Sep. 8, 2015 for International Application No. PCT/US2014/050737.

Third Party Obervation dated Sep. 8, 2015 for International Application No. PCT/US2014/050737.

International Search Report for International Application No. PCT/US2015/039336; Filing Date Jul. 7, 2015.

MP Biomedicals. Lecithin Melting Point Properties. Retrieved Feb. 2016.

* cited by examiner

EXTENDED RELEASE ABUSE DETERRENT LIQUID FILL DOSAGE FORM

CROSS-REFERENCE TO RELATED APPLICATIONS

This application is a Divisional of U.S. patent application Ser. No. 14/918,112 filed Oct. 20, 2015, which claims the benefit of U.S. Provisional Application No. 62/066,298 filed Oct. 20, 2014, the disclosures of each are incorporated herein by reference in their entirety.

FIELD OF THE INVENTION

The present disclosure relates to an oral, extended release, abuse deterrent dosage form. The dosage form contains active pharmaceutical ingredient (API) suspended in a wax matrix which is difficult to extract in order to reduce abuse by non-oral administration routes, e.g. intranasal and/or intravenous. The dosage form also contains a controlled release agent with a relatively low melting temperature, for example, stearoyl polyoxylglyceride and a second agent, for example, polyvinylpyrrolidone (PVP) or a polyethylene glycol (PEG). The low melting temperature allows the controlled release agent to homogenize the API and other excipients within a wax suspension without degrading the API. The composition is designed to allow for extended release of the active ingredient while deterring abuse and maintaining stability of the dosage form at elevated temperatures.

BACKGROUND OF THE INVENTION

FDA-approved drugs are provided in many different forms based on the type of active substance, the indication treated and the preferred route of administration. These forms include enteral formulations (e.g., tablets, capsules or pills), parenteral formulations (e.g., injectable formulations such as intravenous, subcutaneous, intramuscular and intraarticular), liquid formulations (e.g., elixirs), lyophilized formulations and topical formulations. A majority of the FDA-approved drugs are currently available in enteral form, as either a tablet or capsule. Several formulations have been investigated for deterring abuse, either by oral ingestion of the drug with alcohol, or by non-oral administration routes such as intranasal and/or intravenous administration. However a need still exists for extended release abuse deterrent dosage forms.

SUMMARY OF THE INVENTION

The present disclosure relates to an extended release, abuse deterrent capsule including an active substance susceptible to abuse, a controlled release agent, such as a stearoyl polyoxylglyceride, that has a melting temperature less than or equal to about 70° C., and a PEG having an average molecular weight between about 3000 Daltons and about 4000 Daltons or a second agent having a high melting temperature and potentially a high molecular weight, such as a soluble polyvinylpyrrolidone.

The present disclosure also relates to a process for the production of an extended release, abuse deterrent capsule including at least one active substance susceptible to abuse including preparing a homogenized suspension of the at least one active substance susceptible to abuse, a controlled release agent such as a stearoyl polyoxylglyceride that has a melting temperature less than or equal to about 70° C., and a PEG having an average molecular weight between about 3000 Daltons and about 4000 Daltons, or a second agent having a high melting temperature and potentially a high molecular weight, such as a soluble polyvinylpyrrolidone; and dispensing the homogenized suspension into a capsule body to produce the dosage form.

DETAILED DESCRIPTION OF THE INVENTION

Figure 1:
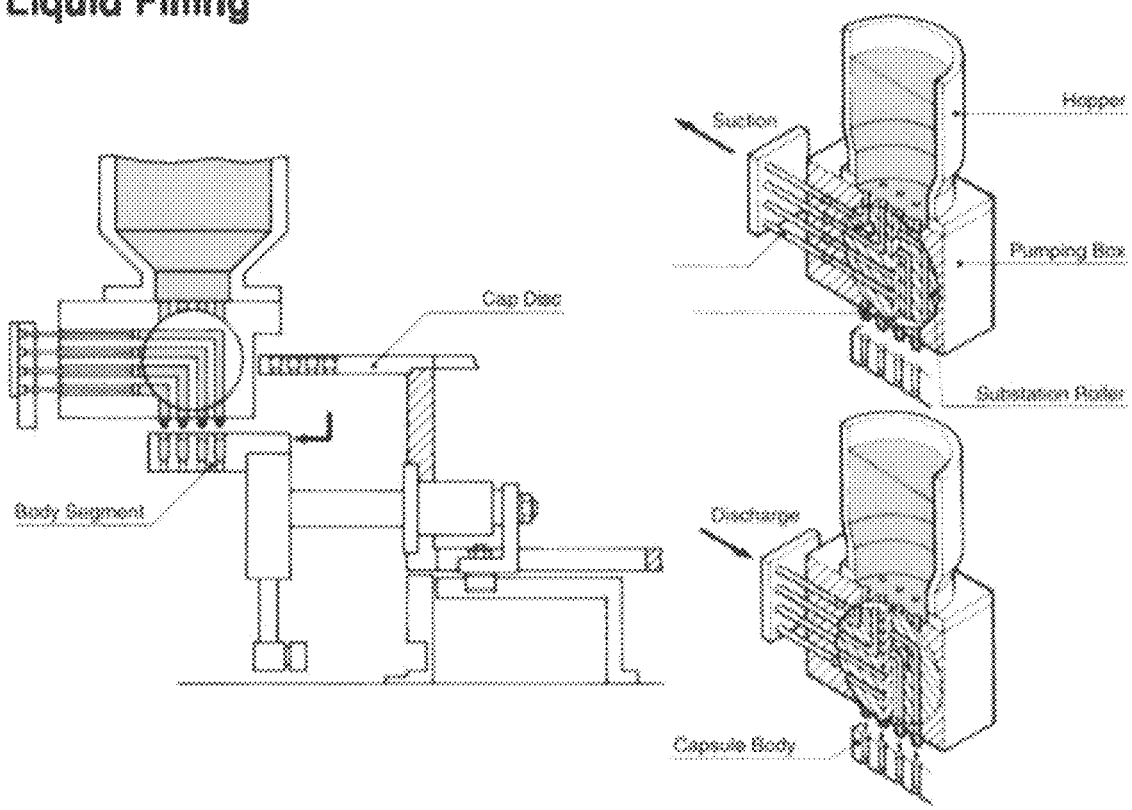
FIG. 1 shows cross sections of a capsule filling machine including the body segment, the cap disc, the hopper, the pumping box, the substation roller, and capsule bodies.

Abuse of prescription drugs, particularly opioids, is a serious and growing public health concern. To address this concern, new formulations are being developed that contain abuse-deterrent properties. Abuse deterrent properties include properties that make product manipulation more difficult or make abuse of the manipulated product less attractive or rewarding.

Recently the FDA issued a guidance for industry related to formulations having abuse deterrent properties. *Guidance for Industry: Abuse-Deterrent Opioids—Evaluation and Labeling*, U.S. Department of Health and Human Services, FDA, CDER, April 2015, the entire contents of which are incorporated herein by reference. These guidelines separate abuse deterrent formulations into six categories, including: physical/chemical barriers, agonist/antagonist combinations, aversion, delivery system, prodrug, or a combination of the aforementioned. As described by the FDA guidance, the categories are:

Physical/Chemical barriers—Physical barriers can prevent chewing, pulverizing, cutting, grating, or grinding. Chemical barriers can resist extraction of the opioid using common solvents like water, alcohol, or other organic solvents. Physical and chemical barriers can change the physical form of an oral drug rendering it less amenable to abuse.

Agonist/Antagonist combinations—An opioid antagonist can be added to interfere with, reduce, or defeat the euphoria associated with abuse. The antagonist can be sequestered and released only upon manipulation of the product. For example, a drug product may be formulated such that the substance that acts as an antagonist is not clinically active when the product is swallowed but becomes active if the product is crushed and injected or snorted.

Aversion—Substances can be combined to produce an unpleasant effect if the dosage form is manipulated prior to ingestion or a higher dosage than directed is used.

Delivery System (including depot injectable formulations and implants)—Certain drug release designs or the method of drug delivery can offer resistance to abuse. For example, a sustained-release depot injectable formulation that is administered intramuscularly or a subcutaneous implant can be more difficult to manipulate.

Prodrug—A prodrug that lacks opioid activity until transformed in the gastrointestinal tract can be unattractive for intravenous injection or intranasal routes of abuse.

Combination—Two or more of the above methods can be combined to deter abuse.

An opioid analgesic submitted for abuse deterrent formulation (ADF) labeling must show conformance to one or more of these categories. The present disclosure relates to an abuse deterrent dosage form for oral administration, which provides extended release of an active pharmaceutical substance and conforms to one or more of these categories. In one embodiment, the abuse deterrent dosage form of the present disclosure conforms to at least one of the six FDA categories. In another embodiment, the abuse deterrent dosage form of the present disclosure conforms to at least two of the six FDA categories. In another embodiment, the abuse deterrent dosage form of the present disclosure conforms to at least three of the six FDA categories. In another embodiment, the abuse deterrent dosage form of the present disclosure conforms to at least four of the six FDA categories. In another embodiment, the abuse deterrent dosage form of the present disclosure conforms to at least five of the six FDA categories.

For example, an abuse deterrent dosage form of the present disclosure can reduce abuse by the incorporation of at least one barrier, e.g., chemical and/or physical barrier. The barrier can be designed to prevent abuse based on extraction and/or purification of the API from the dosage form. Preferably, the barrier prevents or reduces the effectiveness of these methods. As used herein, the phrase "abuse deterrent" means that the active substance cannot readily be separated from the formulation in a form suitable for abuse by such means as, for example, extraction. Abuse deterrent measures render it difficult to transform the dosage form into a purified, abusable powder or extract for non-oral administration, such as intranasal or intravenous.

In one embodiment, the present disclosure relates to an oral, extended release, abuse deterrent dosage form including (a) an active substance susceptible to abuse; (b) a controlled release agent such as a stearoyl polyoxylglyceride that has a melting temperature less than or equal to about 70° C.; and (c) a second agent having a high molecular weight such as a soluble polyvinylpyrrolidone with a nominal K-value of about 90.

In another embodiment, the present disclosure relates to an oral, extended release, abuse deterrent dosage form including (a) an active substance susceptible to abuse; (b) a controlled release agent such as a stearoyl polyoxylglyceride that has a melting temperature less than or equal to about 70° C.; and (c) a polyethylene glycol having an average molecular weight between about 3000 Daltons and about 4000 Daltons.

Active Substance Susceptible to Abuse

As used herein, the term "active substance" or "active substance susceptible to abuse" means any opioid or opioid related compound subject to potential abuse. The active substance may include, without limitation, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, oxymorphone, papvretum, pentazocine, phenadoxone, phenazocine, phenomorphan, phenoperidine, piminodine, propiram, propoxyphene, sufentanil, tilidine, tramadol, tapentadol, and pharmaceutically acceptable salts and mixtures thereof.

In particular embodiments, the active substance can be hydrocodone or oxycodone.

The wt % of the active substance may vary depending on the active substance, stability, release profile and bioavailability. In some embodiments, the dosage form includes at least about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 2 wt %, 2.5 wt %, 3 wt %, 4 wt %, 5 wt %, 6 wt %, 7 wt %, 7.10 wt, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 65 wt %, 69 wt %, 70 wt %, 75 wt %, 80 wt %, 85 wt %, 88 wt %, 90 wt %, or 95 wt % of the active substance. Any of these values may be used to define a range for the wt % of the active substance depending on the application. For example, the amount of active substance in the dosage form may range from about 0.10 wt % to about 60 wt %. Particularly, the amount of active substance in the dosage form may range from about 0.1 wt % to about 1.5 wt %, from about 5 wt % to about 30 wt %, from about 15 wt % to about 20 wt %, from about 15 wt % to about 30 wt %, from about 40 wt % to about 60 wt %, from about 40 wt % to about 50 wt %, or from about 42 wt % to about 46 wt %.

For example, the dosage form may be a 100 mg capsule including about 5 mg, about 10 mg, about 15 mg, about 20 mg, or about 30 mg of active substance (e.g. oxycodone HCl). In other embodiments, the dosage form may be a 150 mg capsule including about 5 mg, about 10 mg, about 15 mg, about 20 mg, about 30 mg, or about 45 mg of active substance (e.g. oxycodone HCl). In other embodiments, the dosage form may be a 200 mg capsule including about 5 mg, about 10 mg, about 15 mg, about 20 mg, about 30 mg, about 40 mg, about 50 mg, about 60 mg, about 70 mg or about 80 mg of active substance (e.g. oxycodone HCl). In other embodiments, the dosage form may be a 250 mg capsule including about 2.5 mg, about 5 mg, about 7.5 mg, about 10 mg, about 15 mg, about 20 mg, about 30 mg, about 45 mg, about 50 mg, about 60 mg, about 70 mg, about 80 mg, about 90 mg or about 100 mg of an active substance (e.g. oxycodone HCl). In other embodiments, the dosage form may be a 275 mg capsule including about 2.5 mg, about 5 mg, about 7.5 mg, about 10 mg, about 15 mg, about 20 mg, about 30 mg, about 45 mg, about 50 mg, about 60 mg, about 70 mg, about 80 mg, about 90 mg or about 100 mg of an active substance (e.g. oxycodone HCl). In other embodiments, the dosage form may be a 500 mg capsule including about 2.5 mg, about 5 mg, about 7.5 mg, about 10 mg, about 15 mg, about 20 mg, about 30 mg, about 45 mg, about 50 mg, about 60 mg, about 70 mg, about 80 mg, about 90 mg or about 100 mg of an active substance (e.g. oxycodone HCl). In other embodiments, the dosage form may be a 700 mg capsule including about 2.5 mg, about 5 mg, about 7.5 mg, about 10 mg, about 15 mg, about 20 mg, about 30 mg, about 45 mg, about 50 mg, about 60 mg, about 70 mg, about 80 mg, about 90 mg or about 100 mg of an active substance (e.g. hydrocodone).

Controlled Release Agent

The controlled release agent may include a compound selected from the group consisting of Compritol® ATO 888 (glyceryl behenate), Compritol® HD5 ATO (behenoyl polyoxylglycerides), Geleol™ mono and di glycerides (glycerol monostearate), and Gelucire® 33/01 (glycerol esters of sat. C8-C18 fatty acids), Gelucire® 39/01 & 43/01 (glycerol esters of sat. C12-C18 fatty acids), Gelucire® 44/14 (lauroyl polyoxylglycerides/PEG-32 glyceryl laurate), Gelucire® 50/13 (stearoyl polyoxylglyceride), Gelucire® 53/10 (PEG-32 glyceryl stearate), Gelucire® 62/02 (saturated polyglycolized glycerides), Precirol® ATO 5 (glyceryl disterate/glyceryl palmitostearate), or Suppocire® pellets (hard fats).

The Gelucire@ molecules are described utilizing a two part number: the first number indicates the melting temperature of the molecule; the second refers to the HLB number or Hydrophilic-Lipophilic Balance number which denotes if the molecule is hydrophobic or hydrophilic. This HLB number ranges from 0-14 with <10 being hydrophobic and >10 being hydrophilic. Hydrophilic molecules work through a swelling and disintegration mechanism of release whereas hydrophilic molecules work though erosion/diffusion. In certain embodiments the Gelucire® molecules used in this present disclosure are hydrophilic. In other embodiments, Gelucire® molecules used in this present disclosure are hydrophobic. In certain embodiments, a combination of hydrophobic and hydrophilic molecules are used.

The total wt % of the controlled release agent in the dosage form may vary depending on the active substance, stability, and release profile. In some embodiments, the controlled release agent is at least about 5 wt %, 10 wt %, 15 wt %, 20 wt %, 25 wt %, 30 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 85 wt %, 88 wt %, 90 wt %, or 95 wt % of the dosage form. Any of these values may be used to define a range for the wt % of the controlled release agent in the dosage form. For example, in some embodiments, the wt % of the controlled release agent in the dosage form ranges from about 15 wt % to about 60 wt % or from about 30 wt % to about 40 wt %.

In certain embodiments, the controlled release agent has a melting temperature of about 100° C., 99° C., 98° C., 97° C., 96° C., 95° C., 94° C., 93° C., 92° C., 91° C., 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., 47° C., 46° C., 45° C., 44° C., 43° C., 42° C., 41° C., 40° C., 39° C., 38° C., 37° C., 36° C., 35° C., 34° C., 33° C., 32° C., 31° C. or 30° C. In certain embodiments, the controlled release agent has a melting temperature that is less than or equal to about 100° C., 99° C., 98° C., 97° C., 96° C., 95° C., 94° C., 93° C., 92° C., 91° C., 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., 47° C., 46° C., 45° C., 44° C., 43° C., 42° C., 41° C., 40° C., 39° C., 38° C., 37° C., 36° C., 35° C., 34° C., 33° C., 32° C., 31° C. or 30° C. Any of these values may be used to define a range for the melting temperature of the controlled release agent. For example, the controlled release agent may have a melting temperature from about 90° C. to about 50° C. or from about 60° C. to about 40° C.

In one embodiment, the controlled release agent melts at a relatively low temperature under a process that incorporates as little oxygen as possible during melting and homogenization. For example, the stearoyl polyoxylglyceride requires a melting temperature of at least 70° C. with incorporation of as little oxygen as possible during melting and homogenization. The melted controlled release agent, and optionally the PEG, can create a suspension which incorporates other components of the dosage form, such as the second agent, which melts at a higher temperature.

Second Agent

The second agent may be selected from the group consisting of hydroxypropyl methylcellulose (HPMC), polyvinyl acetate, polyvinylpyrrolidone, cellulose ethers, cellulose esters, acrylic resins, and derivatives thereof, and combinations thereof. Particularly, the second agent may be selected from ethylcellulose, hydroxypropyl methylcellulose, hydroxypropylcellulose, hydroxymethylcellulose, poly(meth)acrylic acid, polyvinylpyrrolidone and derivatives thereof, such as the salts, amides or esters, and combinations thereof.

The total wt % of the second agent in the dosage form may vary depending on the active substance, stability, and release profile. In some embodiments, the second agent is at least about 5 wt %, 10 wt %, 15 wt %, 20 wt %, 25 wt %, 30 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 85 wt %, 88 wt %, 90 wt %, or 95 wt % of the dosage form. Any of these values may be used to define a range for the wt % of the second agent in the dosage form. For example, in some embodiments, the wt % of the second agent in the dosage form ranges from about 5 wt % to about 60 wt % or from about 10 wt % to about 35 wt %.

In certain embodiments, the second agent has a melting temperature of about 100° C., 110° C., 120° C., 130° C., 135° C., 140° C., 145° C., 150° C., 155° C., 160° C., 165° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C., 410° C., 420° C., 430° C., 440° C., 450° C., 460° C., 470° C., 480° C., 490° C., 500° C., 600° C., 700° C., 800° C., 900° C. or 1000° C. In certain embodiments, the second agent has a melting temperature greater than or equal to about 100° C., 110° C., 120° C., 130° C., 135° C., 140° C., 145° C., 150° C., 155° C., 160° C., 165° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C., 410° C., 420° C., 430° C., 440° C., 450° C., 460° C., 470° C., 480° C., 490° C., 500° C., 600° C., 700° C., 800° C., 900° C. or 1000° C. Any of these values may be used to define a range for the melting temperature of the second agent. For example, the second agent may have a melting temperature from about 100° C. to about 200° C. or from about 135° C. to about 165° C.

In certain embodiments, the dosage form of the present disclosure does not include a second agent.

Polyethylene Glycol

The compositions of the present disclosure can also contain one or more polyethylene glycols. In some embodiments, the PEG has an average molecular weight of 3000, 3050, 3100, 3150, 3200, 3250, 3300, 3350, 3400, 3450, 3500, 3550, 3600, 3650, 3700, 3750, 3800, 3850, 3900, 3950 or 4000 Daltons. Any of these values may be used to define a range for the average molecular weight of the second PEG. For example, the PEG may have an average molecular weight between about 3100 Daltons and about 3900 Daltons, between about 3200 Daltons and about 3800 Daltons, between about 3300 Daltons and about 3700 Daltons, between about 3400 Daltons and about 3600 Daltons, between about 3000 Daltons and 3200 Daltons, between about 3200 Daltons and about 3400 Daltons, between about 3600 Daltons and about 3800 Daltons, or between about 3800 Daltons and about 4000 Daltons.

The total wt % of PEG in the dosage form may vary depending on the active substance, stability, and release profile. In some embodiments, the PEG is at least about 5 wt %, 10 wt %, 15 wt %, 20 wt %, 25 wt %, 30 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 85 wt %, 88 wt %, 90 wt %, or 95 wt % of the dosage form. Any of these values may be used to define a range for the wt % of PEG in the dosage form. For example, in some embodiments, the wt % of PEG in the dosage form ranges from about 30 wt % to about 50 wt % or from about 20 wt % to about 60 wt %.

Dye

The composition can also include one or more dyes. A dye is useful in deterring abuse by discouraging the abuser from intravenous injection. For example, extraction of the dye along with the active ingredient would result in a colored solution that would discourage the abuser from intravenous injection. Thus, in certain embodiments, the dye reduces abuse by extracting and injecting. The dye may be selected from known dyes suitable for use in pharmaceutical formulations or approved by the FDA for such use. For example, the dye may be FD&C Blue No. 2 or a 50/50 Wt % solution of FD&C Blue No. 2 in PEG. In another embodiment, the dye may be a grey dye including FD&C Blue #1, FD&C Yellow #6, and FD&C Red #40. The dye may be in a 90% PEG 3350 blend. In certain embodiments, 14 mg of dye blend is used in each capsule or about 1.4 mg of concentrated dye. In certain embodiments a grey dye is used since it is visually deterring and non-transparent. The dosage form may include about 0.10 wt %, 0.20 wt %, 0.30 wt %, 0.40 wt %, 0.50 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, or 20 wt % dye. Any of these values may be used to define a range for the wt % of the dye. For example, the dosage form may contain between about 0.10 wt % and about 15 wt % dye. Particularly, the dosage form may contain between about 0.20 wt % and about 1.5 wt % dye, about 0.50 wt % and about 1.0 wt % dye, or about 7 to about 14 wt % dye. In certain embodiments, the dosage form may include about 1 mg, 1.4 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg or 30 mg of dye. In another embodiment, the dosage form of the present disclosure excludes a dye.

Other Excipients

The composition can also include a preservative or antioxidant. The preservative or antioxidant reduces or limits the degradation or deterioration of the abuse deterrent dosage form. The addition of a preservative or antioxidant in the dosage form may be necessary to prevent premature degradation of the active substance over the shelf life of the dosage form.

The preservative or antioxidant may be selected from preservatives or antioxidants known to one skilled in the art for use in pharmaceutical formulations, such as citric acid, ascorbic acid, ascorbyl palmitate, butylated hydroxyanisole, butylated hydroxytoluene, erythorbic acid, hypophosphorous acid, lactobionic acid, monothioglycerol, potassium metabisulfite, propyl gallate, racemethionine, sodium bisulfite, sodium formaldehyde sulfoxylate, sodium metabisulfite, sodium sulfite, sodium thiosulfate, stannous chloride, sulfur dioxide and tocopherols. The formulation, or dosage form, may contain between about 0.1 wt % and about 2.0 wt %, or about 0.25 wt % and about 0.75 wt % of preservative or antioxidant. In another embodiment, the dosage form of the present disclosure excludes a preservative or antioxidant.

In some embodiments, the dosage form includes one or more excipients that form a gel in the presence of an alcohol. The alcohol gelling/thickening agent reduces or limits the potential for abuse by preventing extraction of the active substance from the dosage form. For example, when introduced to an alcohol solution, the components of the dosage form (e.g., active substances, stearoyl polyoxylglyceride, PEG, PVP) may become trapped in a gel/viscous liquid which prevents extraction and subsequent alcohol evaporation to produce a pure active substance. In one embodiment, the alcohol gelling/thickening agent does not form a gel in the presence of water. The dosage form may contain between about 0.1 wt % to 40 wt % alcoholic gelling/thickening agent. In another embodiment, the dosage form of the present disclosure does not contain an alcohol gelling/thickening agent.

The alcohol gelling/thickening agent may be a gelling or thickening agent known to one skilled in the art for use in pharmaceutical formulations, such as acacia, alginic acid, bentonite, calcium acetate, carbomers, carboxymethylcellulose, ethylcellulose, gelatin, hydroxyethylcellulose, hydroxypropyl cellulose, magnesium aluminum silicate, methylcellulose, poloxamers, polyvinylpyrrolidone, polyvinyl alcohol, polyvinyl acetate, sodium alginate, sorbitol derivatives, tragacanth, or xanthan gum.

The dosage form may additionally include at least one additive independently selected from surfactants, solubilizers, emulsifiers, bulking agents, poloxamers, lubricants, flavorings or combination thereof.

Abuse Deterrence

One of the most common means of abuse of an orally administered opioid analgesic involves the manipulation of the oral dosage form in order to achieve rapid delivery of the active substance from the dosage form. With regards to extended release formulations, abusers attempt to manipulate the dosage form to cause instantaneous release of the active substance originally intended to be delivered over 6-12 hours. This is a common method taken by abusers referred to as "dose dumping" which can be utilized through decreasing particle size or use of a solvent. Dose dumping results in a rapid release of higher than intended levels of active substance into the body, resulting in a euphoric high. In order for physical manipulation, such as chewing, grinding, or pulverizing, to be used as an effective means of abuse, the original dosage form must be manipulated so as to decrease the particle size of the drug which can be effectively insufflated and/or swallowed. Traditionally, decreasing the particle size of a dosage form will increase the rate of dissolution due to an increase of surface area on which a solution or solvent can act. One way to prevent abuse by physical manipulation is by capturing the active substance susceptible to abuse in a matrix which is dissolved at a similar rate regardless of particle size. This will inhibit abusers from achieving a euphoric high by limiting the amount of active substance available at one time. In some embodiments, the formulation of the present disclosure will maintain an extended release profile regardless of particle size. This delay in the rapid onset of active substance available is thought to decrease abuse by oral, intranasal, and intravenous pathways.

The dosage form of the present disclosure allows for manipulation by chewing, grinding or pulverizing using common equipment, such as a coffee grinder. For example, the formulation of the present disclosure contains no long chain polymers and as a result, can be easily ground into a powdered form. However, the formulation of the present disclosure deters abuse by limiting the amount of active substance available at one time regardless of particle size. The formulation prevents the active substance, or at least substantial portions of the active substance, from being immediately released when introduced to an aqueous environment. As a result, the dosage form is said not to be able to be prepared for abuse via swallowing or insufflation.

The dosage form of the present disclosure can also significantly limit the extraction of the active substance by common solvents (e.g., cold water or distilled aqueous ethanol) from the formulation. For example, the formulation deters abuse by limiting the ability of persons to extract the active substance from the dosage form (either intentionally or unintentionally), such that the active substance cannot easily be concentrated for parenteral administration. For example, if the dosage form is attempted to be extracted with alcohol or an aqueous solution, the stearoyl polyoxylglyceride, PVP, PEG and/or dye or combinations thereof will also be extracted and cannot be separated from the active substance, preventing the preparation of pure drug for intravenous administration. Extraction with a solution would result in a grey/black/brown liquid containing the stearoyl polyoxylglyceride, PVP, PEG, dye or combinations thereof, and the active substance. If an abuser tries to evaporate or burn off the liquid to form a powder, the stearoyl polyoxylglyceride and PEG melt before the alcohol and/or water evaporated, so that the extraction essentially becomes a melted wax with suspended API, which forms a solid once returned to room temperature. This prevents an abuser from separating out the extended release excipients and thereby, allows the dosage form to maintain an extended release profile. These properties allow for an oral drug delivery system that satisfies at least one of the categories in the FDA guidance (e.g., "physical and chemical barriers can change the physical form of an oral drug rendering it less amenable to abuse"). The abuse deterrent dosage form may also include, but does not require, the incorporation of other deterrents such as antagonists or irritants.

In one embodiment, the controlled release agent includes stearoyl polyoxylglyceride. The dosage form of the present disclosure can be rendered abuse deterrent by incorporating stearoyl polyoxylglyceride in the dosage form. The stearoyl polyoxylglyceride can deter extraction of the active substance with an alcohol in order to form a purified powder containing the active substance. For example, since stearoyl polyoxylglyceride melts and forms a wax before the alcohol burns off, an abuser may not be able to obtain a powder containing the active substance. The addition of a PEG to the dosage form may also deter abuse since it is soluble in water and alcohol and melts before either can be flashed off. Addition of a dye to the dosage form may result in a colored solution after extraction of the active substance, deterring intravenous injection. By varying the quantity of stearoyl polyoxylglyceride and/or PVP or PEG present within a dosage form, the characteristics of the dosage form can be manipulated in a way to create a wide array of abuse deterrent capsules having extended release profiles.

The controlled release agent, e.g. stearoyl polyoxylglyceride, can also be capable of allowing extended release of the active substance, providing abuse deterrence, and/or ensuring the formation of a solid dosage form that is stable at elevated temperatures, for example 40° C. The dosage form of the present disclosure can accomplish one or more of the above capabilities by using a mixture of a controlled release agent having a relatively low melting temperature, and a second agent having a relatively high melting temperature or a controlled release agent having a relatively low melting temperature, and/or a PEG. For example, the dosage form can include a controlled release agent having a melting temperature less than or equal to about 70° C., and a high molecular weight PVP or a controlled release agent that has a melting temperature less than or equal to about 70° C., and a PEG having an average molecular weight about 3000 Daltons and 4000 Daltons.

Extended Release

The abuse deterrent composition of the present disclosure is capable of extended release of the active substance. The dosage form may be manufactured to provide a composition exhibiting an extended release profile of at least one active substance. As used herein, "extended release" refers to a dosage form that releases the active substance or a pharmaceutically acceptable salt thereof, into the gastrointestinal tract of the user over a period of 6-12 hours. Particularly, the active substance is released continuously the period of 6-12 hours. In one embodiment, the amount of active substance released from the dosage form, e.g. oxycodone HCl, by exposure to simulated gastric fluid within 6-12 hours is about 85%. The formulation of the present disclosure exhibits an extended release profile that matches the reference listed drug for extended release active substance.

In different embodiments, the amount of active substance released from the dosage form by exposure to simulated gastric fluid, or other dissolution media known to one skilled in the art, is shown in Tables 1 and 2. The values in Tables 1 and 2 represent acceptable USP criterion and may differ from values associated with the RLD specifications. Each individual amount (approx. range) value for each column in Tables 1 and 2 (e.g., 1, 2, 3, 4, 5, 6 and 7) can be used with any other individual amount at other time points to define a release profile.

TABLE 1

Exemplary Release Profiles (e.g. 10, 20, 40, 80 mg active)

| Time (Hours) | 1 Amount (approx. range) | 2 Amount (approx. range) | 3 Amount (approx. range) | 4 Amount (approx. range) | 5 Amount (approx. range) |
|---|---|---|---|---|---|
| 1 | 22% and 28% | 20% and 28% | 22 and 30% | 20% and 30% | 20% and 40% |
| 2 | 37% and 45% | 35% and 45% | 37% and 50% | 35% and 50% | 35% and 55% |
| 4 | 58% and 72% | 55% and 72% | 58% and 75% | 55% and 75% | 55% and 80% |
| 6 | 75% and 80% | 70% and 80% | 75% and 85% | 70% and 85% | 70% and 90% |
| 8 | NLT 75% | NLT 75% | NLT 80% | NLT 80% | NLT 85% |
| 12 | NLT 75% | NLT 80% | NLT 80% | NLT 85% | NLT 90% |

TABLE 2

Exemplary Release Profile

| Time (Hours) | 6 (e.g., 10, 20 and 40 mg active) Amount (approx. range) | 7 (e.g., 80 mg active) Amount (approx. range) |
|---|---|---|
| 1 | 20% and 40% | 25% and 45% |
| 2 | 35% and 55% | 45% and 65% |
| 4 | 55% and 75% | 65% and 85% |
| 6 | 70% and 90% | NLT 80% |
| 8 | NLT 80% | |

Process

In another embodiment, the present disclosure relates to a process for the production of an oral, extended release, abuse deterrent dosage form including preparing a homogenized suspension of at least one active substance susceptible to abuse, a controlled release agent, and a second agent and/or a PEG. The PEG can have an average molecular weight between about 3000 Daltons and about 4000 Daltons. The controlled release agent can have a melting temperature of less than or equal to 70° C. The second agent can have a melting temperature greater than or equal to 100° C. The process can further include dispensing the homogenized suspension into a capsule to produce the dosage form. In some embodiments, the capsule is formed by joining a capsule body with a capsule cap. In some embodiments of the processes described herein, the active substance is hydrocodone. In other embodiments, the active substance is oxycodone HCl. In certain embodiments, the abuse deterrent dosage forms of the present disclosure are capsules. The abuse deterrent dosage forms of the present disclosure may be produced by liquid filled encapsulation. Liquid filled encapsulation is a process in which active pharmaceutical ingredients are suspended or emulsified in a carrier matrix and filled into capsules. The capsules are usually made of hard gelatin or hydroxypropyl methylcellulose. One of the advantages of this dosage form is that it requires fewer excipients and processing steps than other traditional compressed solid dosage forms. The internal solid phase active pharmaceutical ingredient (e.g. oxycodone or hydrocodone) can be suspended in an external fluid phase. (e.g., a stearoyl polyoxylglyceride and/or PEG). In one embodiment, stearoyl polyoxylglycerides are used to liquid fill capsules because they are thermoplastics that melt at temperatures below the melting point of the hard gelatin capsule (<70° C.) and are solids at room temperature. If the filling material is liquid at room temperature, a banding process would need to follow. This process adds a gelatin band around the point where the two capsule ends join to create a unified capsule body to prevent any leakage. In some embodiments, the formulation of the present disclosure can include a band.

An exemplary liquid fill process is described. The liquid fill process can begin by dispensing excipients (e.g., stearoyl polyoxylglyceride, PVP, PEG and stabilizers/preservatives) and API according to theoretical percent weights of the final capsule fill weight. Following this step, the controlled release agent, e.g. stearoyl polyoxylglyceride pellets, can be added to a homogenizing mixing kettle which heats them above their melting point via jacketing on the kettle. When the controlled release agent, e.g. stearoyl polyoxylglyceride, is completely fluid, the API and other excipients can be mixed in to form a homogenized suspension. This occurs with the aid of mechanical agitation by way of several internal stirring arms and the homogenizer built into the kettle. Once a homogenized suspension is attained (newer kettles can be equipped with NIR probes to indicate when this occurs), the suspension can be pumped through jacketed hoses (to maintain the internal kettle temperature to prevent solidification in the hose) to a hopper on the capsule filling machine. An illustration of a capsule filling machine is provided in FIG. 1. The capsule filling hopper can also be jacketed to heat the suspension to prevent solidification. The capsule filling machine can contain a separate hopper which operators can fill with hard gelatin capsules. The hopper can feed into a rectifying drum which aligns all capsules in the same direction. Once aligned, the capsules sit vertically in a cap disk which allows for separation of the body and cap via vacuum. To fill the capsule, a positive displacement piston pump can be used to draw the product in from the jacketed hopper and dispense the suspension into the capsule body through a set of changeable nozzles. Fill weight adjustment can be achieved by varying the piston stroke of the pump. Changes can be made throughout the process due to accommodate frequent in-process capsule weight checks.

Once the capsule body is filled, the capsule body and cap can be joined via pusher pins which raise the capsule body upwards and into the capsule cap, which are held in place above the capsule body by a joining block. The pusher pins then push the unified capsule out of the cap disk and are discharged from the machine. The capsules are allowed to cool at room temperature on trays and are each weight checked via a capsule weigh checking machine. Following this, the capsules are then placed into a final output drum. Automatic capsule filling machines have the ability to produce 500 to 150,000 capsules an hour with a very high degree of accuracy.

In some embodiments, the present disclosure relates to a dosage form as described herein prepared by filling a capsule body with a heated homogenized suspension including an active substance, a controlled release agent, a second agent and/or a PEG. In some embodiments, the homogenized suspension including an active substance, a controlled release agent, and a second agent and/or a PEG wherein the suspension melts at a temperature of about 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., or 90° C. Any of these values may be used to define a range of melting temperatures for the homogenized suspension. For example, in certain embodiments, the homogenized suspension has a melting temperature between about 47° C. and about 52° C. In particular embodiments, the homogenized suspension including an active substance, a controlled release agent, a second agent and/or a PEG melts at temperatures below 77° C., i.e. the melting point of the hard gelatin capsule. In another embodiment, the present disclosure relates to a method of treating pain including administering to an individual in need thereof a therapeutically effective amount of a dosage form as described herein. The dosage form provides rapid onset of analgesia for the treatment of moderate to severe pain.

The disclosures of all cited references including publications, patents, and patent applications are expressly incorporated herein by reference in their entirety. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1—Extended Release ADF Oxycodone Hydrochloride Liquid Fill Capsules with PEG Extended release ADF Oxycodone Hydrochloride liquid fill capsules including stearoyl polyoxylglyceride or glycerol ester of sat. C12-18 fatty acids, and PEG 3350 were prepared and the release profiles of the oxycodone were determined. The capsules were prepared using the following exemplary procedure. Stearoyl polyoxylglyceride or glycerol ester of sat. C12-18 fatty acids, PEG 3350 and grey dye were placed in a 150 mL stainless steel cup on a hot plate, and allowed to melt completely under nitrogen blanket with no agitation, Once melted, citric acid and Oxycodone HCl (and other components, if present) were slowly added and mixed in. Once the necessary minimum melt temperature of 70° C. was achieved, the melt was homogenized using a Silverson homogenizer for a minimum of 10 minutes at setting 5 under a nitrogen blanket. Following homogenization, the melt was allowed to cool to <75° C. Capsules were hand filled to weight using a metal spatula. The melt was left on the hot plate to maintain liquid state. The filled capsules and remaining melt were allowed to cool and weights of good capsules and waste recorded. Table 3 list the formulations prepared.

TABLE 3

Oxycodone Hydrochloride liquid fill capsules.

| Component | Wt % 1 | Wt % 2 | Wt % 3 | Wt % 4 | Wt % 5 | Wt % 6 | Wt % 7 |
|---|---|---|---|---|---|---|---|
| Oxycodone | 5 | 20 | 40 | 40 | 40 | 40 | 29.63 |
| Stearoyl polyoxylglyceride | 87 | 72 | 52 | 0 | 0 | 0 | 52 |
| glycerol ester of sat. C12-18 fatty acids | 0 | 0 | 0 | 52 | 42 | 32 | 0 |
| PEG 3350 | 0 | 0 | 0 | 0 | 10 | 20 | 12.19 |
| Grey Dye Blend | 7 | 7 | 7 | 7 | 7 | 7 | 5.18 |
| Citric Acid | 1 | 1 | 1 | 1 | 1 | 1 | 1 |
| Active, mg | 10 | 40 | 80 | 80 | 80 | 80 | 80 |
| Capsule Fill Wt, mg | 200 | 200 | 200 | 200 | 200 | 200 | 270 |

Dissolution Testing

The extended release ADF oxycodone hydrochloride liquid fill capsules in Table 3 were tested for dissolution. Dissolution testing was performed with reference to USP Monograph on Oxycodone Hydrochloride Extended-Release Tablets. These tests were performed on a dissolution apparatus utilizing UPS <711> Apparatus I (Baskets), with 900 mL Simulated Gastric Fluid (no enzymes) as media and a basket speed of 100 rpm. A 1.5 mL sample was pulled at each evaluated time point and submitted for HPLC analysis. HPLC conditions were modified from the USP monograph in order to observe the release of oxycodone HCl. The HPLC conditions were as follows: Injection Volume: 30 μL (oxycodone); Flow Rate 1.7 mL/min (oxycodone); Detection: UV at 225 nm (oxycodone); Column Temp: 25° C.; Autosampler Temperature: ambient; Gradient: Isocratic; and Runtime: 5 minutes. The specifications for dissolution testing are shown in Tables 1 and 2. The release profiles are shown in the Table 4.

TABLE 4

Dissolution testing of Oxycodone Hydrochloride liquid fill capsules (Average of 3 capsules)

| Formulation | 1 Hour | 4 Hour | 12 Hour |
|---|---|---|---|
| 1 | 28.30 | 78.19 | 90.61 |
| 2 | 35.03 | 99.93 | 105.86 |
| 3 | 46.26 | 101.08 | 101.39 |
| 4 | 3.33 | 6.11 | 11.46 |
| 5 | 3.49 | 21.24 | 36.09 |
| 6 | 14.35 | 80.33 | 102.56 |
| 7 | 30.73 | 81.96 | 102.09 |

Example 2—Extended Release ADF Oxycodone Hydrochloride Liquid Fill Capsules with HPMC Additional formulations containing HPMC in place of PEG were evaluated to determine the effect of HPMC on the active release profiles. The formulations were prepared using the same procedure of Example 1. The formulations are shown in Table 5. The release profiles are shown in the Table 6.

TABLE 5

Oxycodone Hydrochloride liquid fill capsules.

| Component | Wt % 8 | Wt % 9 | Wt % 10 | Wt % 11 | Wt % 12 | Wt % 13 |
|---|---|---|---|---|---|---|
| Oxycodone | 5 | 5 | 5 | 5.714 | 5.714 | 5.714 |
| Stearoyl polyoxylglyceride | 82 | 77 | 72 | 85.286 | 85.286 | 85.286 |
| HPMC | 5 | 10 | 15 | 0 | 5 | 10 |
| Grey Dye Blend | 7 | 7 | 7 | 8 | 8 | 8 |
| Citric Acid | 1 | 1 | 1 | 1 | 1 | 1 |
| Active, mg | 10 | 10 | 10 | 10 | 10 | 10 |
| Capsule Fill Wt, mg | 200 | 200 | 200 | 175 | 175 | 175 |

TABLE 6

Dissolution testing of Oxycodone Hydrochloride liquid fill capsules (Average of 3 capsules)

| Formulation | 1 Hour | 4 Hour | 12 Hour |
|---|---|---|---|
| 8 | 28.41 | 71.53 | 91.56 |
| 9 | 25.85 | 57.03 | 92.41 |
| 10 | 24.64 | 56.08 | 95.97 |
| 11 | 26.93 | 72.39 | 89.98 |
| 12 | 25.62 | 68.55 | 89.14 |
| 13 | 24.65 | 55.14 | 95.20 |

Example 3—Extended Release ADF Oxycodone Hydrochloride Liquid Fill Capsules with HPMC and PEG 35,000

Additional formulations containing HPMC and PEG 35,000 were evaluated to determine the effect of HPMC and PEG 35,000 on release profiles. The formulations were prepared using the same procedure of Example 1. The formulations are shown in Table 7. The release profiles are shown in the Table 8.

TABLE 7

Oxycodone Hydrochloride liquid fill capsules.

| Component | Wt % 14 | Wt % 15 | Wt % 16 | Wt % 17 | Wt % 18 |
|---|---|---|---|---|---|
| Oxycodone | 5 | 5 | 5 | 5 | 5 |
| Stearoyl polyoxylglyceride | 72 | 69.5 | 67 | 64.5 | 62 |
| HPMC | 10 | 10 | 10 | 10 | 10 |
| PEG 35,000 | 5 | 7.5 | 10 | 12.5 | 15 |
| Grey Dye Blend | 7 | 7 | 7 | 7 | 7 |
| Citric Acid | 1 | 1 | 1 | 1 | 1 |
| Active, mg | 10 | 10 | 10 | 10 | 10 |
| Capsule Fill Wt, mg | 200 | 200 | 200 | 200 | 200 |

TABLE 8

Dissolution testing of Oxycodone Hydrochloride liquid fill capsules (Average of 3 capsules)

| Formulation | 1 Hour | 4 Hour | 12 Hour |
|---|---|---|---|
| 14 | 22.95 | 57.51 | 95.62 |
| 15 | 20.55 | 61.23 | 101.46 |
| 16 | 19.94 | 65.35 | 103.32 |
| 17 | 17.58 | 66.51 | 108.84 |
| 18 | 19.17 | 68.23 | 105.68 |

Example 4—Extended Release ADF Oxycodone Hydrochloride Liquid Fill Capsules with HPMC and PEG 3350

Additional formulations containing HPMC and PEG 3350 were evaluated to determine the effect of HPMC and PEG 3350 on release profiles. The formulations were prepared using the same procedure of Example 1. The formulations are shown in Table 9. The release profiles are shown in the Table 10.

TABLE 9

Oxycodone Hydrochloride liquid fill capsules.

| Component | Wt % 19 | Wt % 20 | Wt % 21 | Wt % 22 | Wt % 23 | Wt % 24 | Wt % 25 | Wt % 26 |
|---|---|---|---|---|---|---|---|---|
| Oxycodone | 5 | 5 | 5 | 5 | 5 | 5 | 5 | 5 |
| Stearoyl polyoxylglyceride | 72 | 67 | 62 | 57 | 52 | 47 | 42 | 37 |
| HPMC | 10 | 10 | 10 | 10 | 10 | 10 | 10 | 10 |
| PEG 3350 | 5 | 10 | 15 | 20 | 25 | 30 | 35 | 40 |
| Grey Dye Blend | 7 | 7 | 7 | 7 | 7 | 7 | 7 | 7 |
| Citric Acid | 1 | 1 | 1 | 1 | 1 | 1 | 1 | 1 |
| Active, mg | 10 | 10 | 10 | 10 | 10 | 10 | 10 | 10 |
| Capsule Fill Wt, mg | 200 | 200 | 200 | 200 | 200 | 200 | 200 | 200 |

TABLE 10

Dissolution testing of Oxycodone Hydrochloride liquid fill capsules (Average of 3 capsules)

| Formulation | 1 Hour | 4 Hour | 12 Hour |
|---|---|---|---|
| 19 | 20.63 | 61.75 | 110.46 |
| 20 | 24.48 | 61.57 | 101.33 |
| 21 | 24.30 | 59.86 | 98.97 |
| 22 | 26.65 | 65.27 | 101.18 |
| 23 | 26.75 | 76.50 | 100.32 |
| 24 | 29.08 | 87.03 | 101.63 |
| 25 | 41.36 | 94.98 | 100.25 |
| 26 | 53.34 | 98.33 | 101.71 |

Example 5—Extended Release ADF Oxycodone Hydrochloride Liquid Fill Capsules with HPMC and PEG 3350

Additional formulations containing higher amounts of HPMC were evaluated to determine the effect of higher amounts of HPMC on release profiles. The formulations were prepared using the same procedure of Example 1. The formulations are shown in Table 11. The release profiles are shown in the Table 12.

TABLE 11

Oxycodone Hydrochloride liquid fill capsules.

| Component | Wt % 27 | Wt % 28 | Wt % 29 | Wt % 30 |
|---|---|---|---|---|
| Oxycodone | 5 | 5 | 5 | 5 |
| Stearoyl polyoxylglyceride | 37 | 32 | 32 | 27 |
| HPMC | 15 | 20 | 15 | 20 |

TABLE 11-continued

Oxycodone Hydrochloride liquid fill capsules.

| Component | Wt % 27 | Wt % 28 | Wt % 29 | Wt % 30 |
|---|---|---|---|---|
| PEG 3350 | 35 | 35 | 40 | 40 |
| Grey Dye Blend | 7 | 7 | 7 | 7 |
| Citric Acid | 1 | 1 | 1 | 1 |
| Active, mg | 10 | 10 | 10 | 10 |
| Capsule Fill Wt, mg | 200 | 200 | 200 | 200 |

TABLE 12

Dissolution testing of Oxycodone Hydrochloride liquid fill capsules (Average of 3 capsules)

| Formulation | 1 Hour | 4 Hour | 12 Hour |
|---|---|---|---|
| 27 | 26.54 | 66.50 | 104.11 |
| 28 | 27.86 | 67.73 | 100.10 |
| 29 | 32.88 | 74.41 | 98.08 |
| 30 | 29.06 | 75.94 | 103.35 |

Formulation 29 was further tested using the manufacturing process described in Example 1. The capsules were evaluated for dissolution to determine the effect of the formulations on oxycodone release profiles. The release profiles are shown in the Table 13.

TABLE 13

Dissolution testing of Oxycodone Hydrochloride liquid fill capsules - Formulation 29 - (Average of 6 capsules)

| 10 mg ER Oxycodone | | | Average |
|---|---|---|---|
| 1 Hour | Capsule 1 | 32.461 | 31.13267 |
| | Capsule 2 | 29.899 | |
| | Capsule 3 | 32.632 | |
| | Capsule 4 | 35.324 | |
| | Capsule 5 | 29.656 | |
| | Capsule 6 | 26.824 | |
| 2 Hour | Capsule 1 | 48.661 | 48.032 |
| | Capsule 2 | 46.852 | |
| | Capsule 3 | 49.806 | |
| | Capsule 4 | 51.354 | |
| | Capsule 5 | 48.800 | |
| | Capsule 6 | 42.716 | |
| 3 Hour | Capsule 1 | 61.805 | 63.325 |
| | Capsule 2 | 61.233 | |
| | Capsule 3 | 63.324 | |
| | Capsule 4 | 64.731 | |
| | Capsule 5 | 62.759 | |
| | Capsule 6 | 66.097 | |
| 4 Hour | Capsule 1 | 74.006 | 75.886 |
| | Capsule 2 | 74.172 | |
| | Capsule 3 | 75.773 | |
| | Capsule 4 | 76.900 | |
| | Capsule 5 | 75.773 | |
| | Capsule 6 | 78.689 | |
| 12 Hour | Capsule 1 | 101.092 | 101.0475 |
| | Capsule 2 | 102.867 | |
| | Capsule 3 | 93.646 | |
| | Capsule 4 | 102.077 | |
| | Capsule 5 | 101.977 | |
| | Capsule 6 | 104.626 | |

Table 14 provides exemplary formulations for 20 mg, 40 mg and 80 mg doses of oxycodone.

TABLE 14

Exemplary formulations of extended release 20 mg, 40 mg, and 80 mg ADF Oxycodone Hydrochloride liquid fill capsules

| Oxycodone Dose | Oxycodone HCl % | stearoyl polyoxylglyceride % | PEG 3350 % | HPMC % | Citric Acid % | Grey Dye Blend % | Capsule Fill (mg) |
|---|---|---|---|---|---|---|---|
| 20 mg | 10.00 | 27.00 | 40.00 | 15.00 | 1.00 | 7.00 | 200.00 |
| 40 mg | 16.00 | 19.90 | 42.50 | 15.00 | 1.00 | 5.60 | 250.00 |
| 40 mg | 16.00 | 17.40 | 45.00 | 15.00 | 1.00 | 5.60 | 250.00 |
| 80 mg | 16.00 | 30.20 | 40.00 | 10.00 | 1.00 | 2.80 | 500.00 |
| 80 mg | 16.00 | 55.20 | 15.00 | 10.00 | 1.00 | 2.80 | 500.00 |

Example 6—Extended Release ADF Oxycodone Hydrochloride Liquid Fill Capsules with PVP or PEG 3350

Additional formulations containing PVP or PEG 3350 were evaluated to determine the effect on release profiles. The formulations were prepared using the same procedure of Example 1. The formulations are shown in Table 15. The release profiles are shown in the Table 16.

TABLE 15

Oxycodone Hydrochloride liquid fill capsules.

| Component | Wt % 31 | Wt % 32 | Wt % 33 | Wt % 34 |
|---|---|---|---|---|
| Oxycodone | 4 | 8 | 14.55 | 16 |
| Stearoyl polyoxylglyceride | 69.40 | 65.40 | 66.86 | 45.20 |
| Kollidon 90F (PVP) | 20 | 20 | 12.5 | 0 |
| PEG 3350 | 0 | 0 | 0 | 35 |
| Grey Dye Blend | 5.6 | 5.6 | 5.09 | 2.8 |
| Citric Acid | 1 | 1 | 1 | 1 |

TABLE 15-continued

Oxycodone Hydrochloride liquid fill capsules.

| Component | Wt % 31 | Wt % 32 | Wt % 33 | Wt % 34 |
|---|---|---|---|---|
| Active, mg | 10 | 20 | 40 | 80 |
| Capsule Fill Wt, mg | 250 | 250 | 275 | 500 |

TABLE 16

Dissolution testing of Oxycodone Hydrochloride liquid fill capsules (Average of 3 capsules)

| Formulation | 1 Hour | 2 Hour | 4 Hour | 6 Hour | 8 Hour |
|---|---|---|---|---|---|
| 31 | 27.58 | 42.61 | 63.78 | 79.89 | 90.85 |
| 32 | 26.53 | 40.68 | 62.25 | 78.84 | 90.42 |
| 33 | 27.24 | 42.55 | 65.88 | 84.16 | 93.75 |
| Specification (10, 20, 40 mg) | 20%-40% | 35%-55% | 55%-75% | 70%-90% | >85% |
| 34 | 30.71 | 53.00 | 80.43 | 97.22 | N/A |
| Specification (80 mg) | 25%-45% | 45%-65% | 65%-85% | >85% | N/A |

The 10, 20, and 40 mg formulations of 31-33 are similar and contain a controlled release agent (e.g., stearoyl polyoxylglyceride) and a second agent (PVP). The second agent can also act to decrease purity since it can be soluble in both water and ethanol, as well as to slow dissolution in the presence of the controlled release agent. Kollidon 90F is a high molecular weight polyvinylpyrrolidone. The 90 is a nominal value that is a calculated by the manufacturer based on viscosity and molecular weight.

The 80 mg formulation contains only the controlled release agent and PEG 3350. The second agent was excluded because in order to reach a processable viscosity the fill weight had to be increased to 500 mg. In some embodiments, a processable viscosity is less than about 2500 cP at 75° C. measured using a Brookfield RVDV-II+ Pro digital viscometer equipped with a RV3 spindle at 50 RPM. This made the resulting capsule slug larger and delayed the release dramatically with the controlled release agent alone. The PEG was added to speed up the dissolution to achieve the necessary endpoints. The PEG also decreases the purity.

In other embodiments, a processable viscosity is less than about 2500, 2400, 2300, 2200, 2100, 2000, 1900, 1800, 1700, 1600, 1500, 1400, 1300, 1200, 1100, 1000, 900, 800, 700, 600 or about 500 cP at 75° C. measured using, for example, a Brookfield RVDV-II+ Pro digital viscometer equipped with a RV3 spindle at 50 RPM. These values can be used to define a range, such as between about 1500 and about 2000 cP at 75° C.

Example 7—Evaluation of Dyes

Figure 2A:
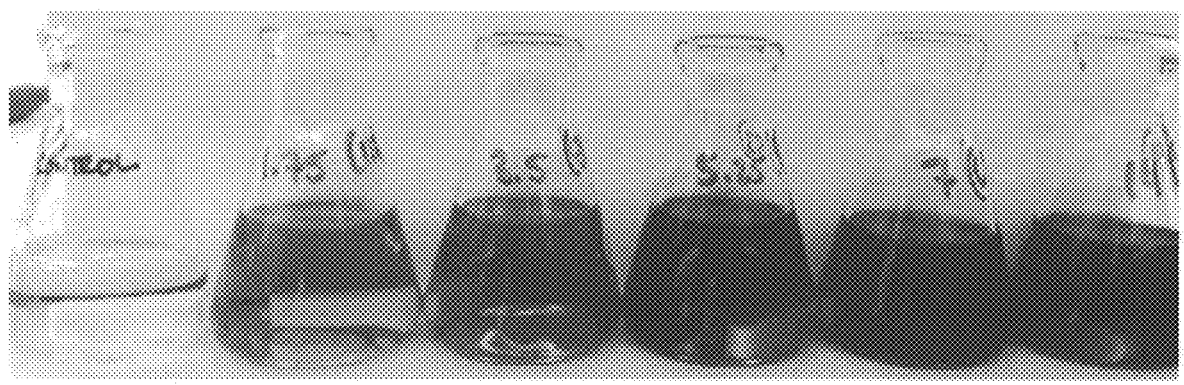
FIG. 2A shows solutions of grey dye before filtering.
Figure 2B:
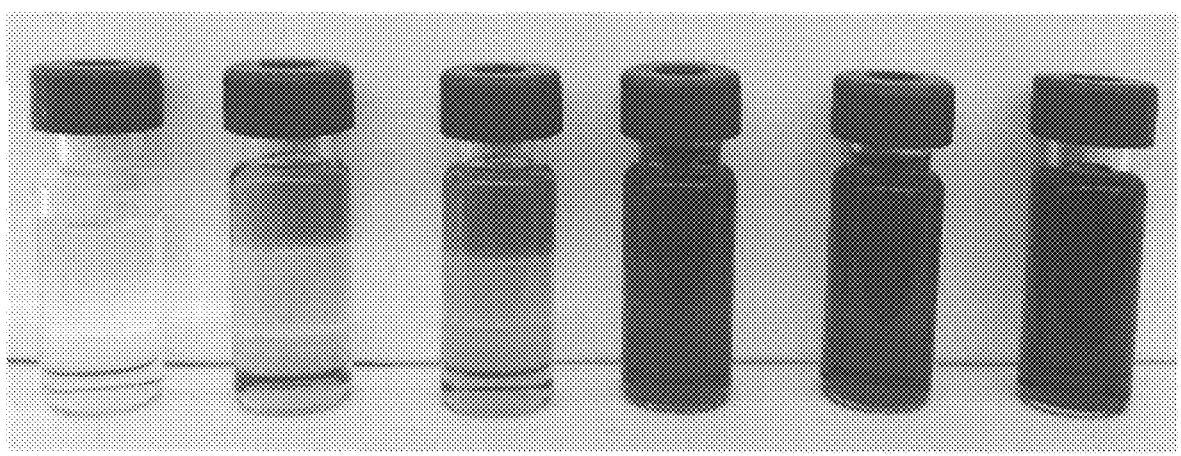
FIG. 2B shows solutions of grey dye after filtering.

Numerous dyes were evaluated for their potential to deter intravenous abuse. Varying concentrations of FD&C Blue #2, green (FD&C Blue #2 and FD&C Yellow #5), FD&C Yellow #5, FD&C Red #40, and grey dye (FD&C Blue #1, FD&C Yellow #6, FD&C Red #40) were evaluated by dissolving them in a 95% ethanol 5% purified water (190 proof) solution and passing the solution through a syringe filter. After syringe filtering the dye solutions were visually evaluated for color intensity and rated on a scale of 0 to 5, with 0 indicating no color and 5 indicating dark, significant color. As shown in Table 15 below, the blue and green dyes exhibited the highest color intensity at low concentrations, e.g. 0.25% w/w. Solutions of grey dye before and after filtering are shown in FIGS. 2A and 2B, respectively. The grey dye was particularly striking and less appealing. An acceptable color scale designation after extraction of the dye is ≥4 on a scale of 1 to 5, with 5 being the highest level of color.

TABLE 17

Color intensity of dye solutions after syringe filtering

| Batch Number | Dye Color | Dye (% w/w) | Dye (mg) | Color Number Assignment* |
|---|---|---|---|---|
| 66 | Blue | 0.25 | 1.75 | 4 |
| 67 | Blue | 0.50 | 3.50 | 5 |
| 68 | Blue | 0.75 | 5.25 | 5 |
| 69 | Blue | 1.00 | 7.00 | 5 |
| 70 | Green | 0.25 | 1.75 | 4 |
| 71 | Green | 0.50 | 3.50 | 4 |
| 72 | Green | 0.75 | 5.25 | 4 |
| 73 | Green | 1.00 | 7.00 | 4 |
| 74 | Yellow | 0.25 | 1.75 | 3 |
| 75 | Yellow | 0.50 | 3.50 | 4 |
| 76 | Yellow | 0.75 | 5.25 | 5 |
| 77 | Yellow | 1.00 | 7.00 | 5 |
| 78 | Red | 0.11 | 0.75 | 2 |
| 79 | Red | 0.21 | 1.50 | 3 |
| 80 | Red | 0.43 | 3.00 | 4 |
| 81 | Red | 0.63 | 4.44 | 5 |
| 82 | Grey | 0.25 | 1.75 | 2 |
| 83 | Grey | 0.50 | 3.50 | 2 |
| 84 | Grey | 0.75 | 5.25 | 4 |
| 85 | Grey | 1.00 | 7.00 | 4 |
| 86 | Grey | 2.00 | 14.00 | 5 |

Example 8—Abuse Deterrent Properties of Extended Release Liquid Fill Capsule Oxycodone Formulations Grinding—

The purpose of grinding or chewing an extended release dosage form is to break the extended release properties of the dosage form and cause the active substance to "dump" or be released in a relatively short amount of time. This is a common method of abuse since it requires little to no equipment to perform by an abuser. Once chewed or ground, the drug can be swallowed or insufflated for immediate release of the active substance.

The purpose of this study was to show that the contents of the capsule can maintain extended release properties and prevent dose dumping regardless of particle size in order to prevent abuse or misuse of the dosage form. The Retsch Knife Mill GRINDOMIX GM200 (TE96) was utilized to mimic a commercially available coffee grinder (Mr. Coffee) in order to grind the drug product from a capsule slug into a powder. The powder was then subjected to dissolution testing similar to that of the intact capsule. For the purposes of this study, any resulting powder which achieves a large increase (i.e., double that of the original intact formulation) in dissolution versus the intact capsule at the 1 or 2 hour mark is considered suitable for intranasal or oral abuse.

The Retsch Knife Mill GRINDOMIX GM200 utilizes a circular blade attachment to mimic commercially available coffee grinders. The GM200 has a top speed of 10,000 revolutions per minute (rpm), while commercially available coffee grinders have a top speed of approximately 20,000 rpm (an approximate two-fold increase in speed when comparing the GM200 to a Mr. Coffee grinder). However, the approximate two-fold increase in blade diameter (118 mm vs. 60 mm, when comparing the GM200 to a Mr. Coffee grinder, respectively) compensates for the approximate two-fold decrease in top speed via the inversely proportional relationship of the two variables. Further, the torque provided by the GM200 is significantly higher than the torque provided by a Mr. Coffee grinder (0.860 Nm (Newton meters) of the GM200 vs. 0.062 Nm of the Mr. Coffee grinder, respectively), which additionally illustrates the ability (or lack thereof) of the Mr. Coffee grinder to modify the drug products into a particle size suitable for intranasal or oral abuse. The study evaluated the difference in dissolution of ground forms of several different formulations of oxycodone following modification (grinding) by the GM200.

Experimental

The following test equipment was used: Retsch Knife Mill GRINDOMIX GM200 (TE96). The following testing conditions were used: Analysis speed: 10,000 rpm; Analysis time: 30 seconds; The capsules, the formulations of which are listed in Table 18, are emptied prior to grinding (grinding the capsule in addition to the fill is unnecessary and not indicative of the pathway utilized by an abuser). Approximately 5.0 g of emptied capsules were used to create the powder. A tared empty capsule was then filled with the powder to +/−5 mg of the original intact capsule fill weight. Each sample was prepared in triplicate (N=3) and averaged to achieve a percent drug dissolved at a given time point. The results are shown in Table 19 and FIGS. 5-8.

TABLE 18

Oxycodone Hydrochloride liquid fill capsules.

| Component | Wt % 31 | Wt % 33 | Wt % 34 | Wt % 35 | Wt % 4-5 |
|---|---|---|---|---|---|
| Oxycodone | 4 | 14.55 | 16 | 16 | 29.09 |
| Stearoyl polyoxylglyceride | 69.40 | 66.86 | 45.20 | 60.20 | 17.32 |
| glycerol ester of sat. C12-18 fatty acids | 0 | 0 | 0 | 0 | 47.50 |
| Kollidon 90F (PVP) | 20 | 12.5 | 0 | 0 | 0 |
| PEG 3350 | 0 | 0 | 35 | 20 | 0 |
| Grey Dye Blend | 5.6 | 5.09 | 2.8 | 2.8 | 5.09 |
| Citric Acid | 1 | 1 | 1 | 1 | 1 |
| Active, mg | 10 | 40 | 80 | 80 | 80 |
| Capsule Fill Wt, mg | 250 | 275 | 500 | 500 | 275 |

TABLE 19

Grinding data for the Extended Release Liquid Fill Capsule Oxycodone Formulations

| Batch | Potency | Intact/Ground | 1 h | 2 h | 4 h | 6 h | 8 h |
|---|---|---|---|---|---|---|---|
| 35 | 80 mg | Intact | 28 | 51 | 80 | 97 | N/A |
| | | Ground | 51 | 78 | 99 | 100 | |
| | | Difference | 23 | 27 | 20 | 2 | |
| 34 | 80 mg | Intact | 23 | 40 | 61 | 77 | N/A |
| | | Ground | 37 | 59 | 88 | 100 | |
| | | Difference | 14 | 19 | 26 | 23 | |
| 31 | 10 mg | Intact | 27 | 41 | 62 | 79 | 90 |
| | | Ground | 37 | 58 | 82 | 93 | 96 |
| | | Difference | 11 | 17 | 19 | 14 | 5 |

TABLE 19-continued

Grinding data for the Extended Release Liquid Fill Capsule Oxycodone Formulations

| Batch | Potency | Intact/Ground | 1 h | 2 h | 4 h | 6 h | 8 h |
|---|---|---|---|---|---|---|---|
| 33 | 40 mg | Intact | 27 | 43 | 66 | 84 | 94 |
| | | Ground | 39 | 61 | 87 | 97 | 99 |
| | | Difference | 12 | 19 | 21 | 13 | 5 |

As shown in Table 19 and FIG. 5-8, the ground capsule does slightly increase the rate of dissolution. The active substance, however, does not "dump" because the increase is less than a 2 fold increase in the early time points (e.g. 1 h and 2 h). The ground formulations still maintain an sustained release profile. The dosage form has a deterrent to abuse at least by physical manipulation such as chewing, grinding, or pulverization.

Extraction—

Color is one identifying characteristic of commercial drug products. Color can be applied to the dosage form in two ways: dye or coating. High potency alcohol (i.e., ≥90 proof (95%)) is one extraction solvent that can be used by abusers for APIs which are insoluble in water or in order to separate the API from other water soluble excipients. Dyes or coatings can potentially be used to alter the physical appearance of the extracted solution of drug product (i.e., turn the resulting solution a noticeable color).

Accordingly, the inclusion of one or more dyes in a drug formulation is one method to render a formulation abuse deterrent. Significant discoloration of an extraction product from a formulation subject to abuse can discourage a potential abuser from using (e.g., injecting or ingesting) the extraction product.

Figure 3:
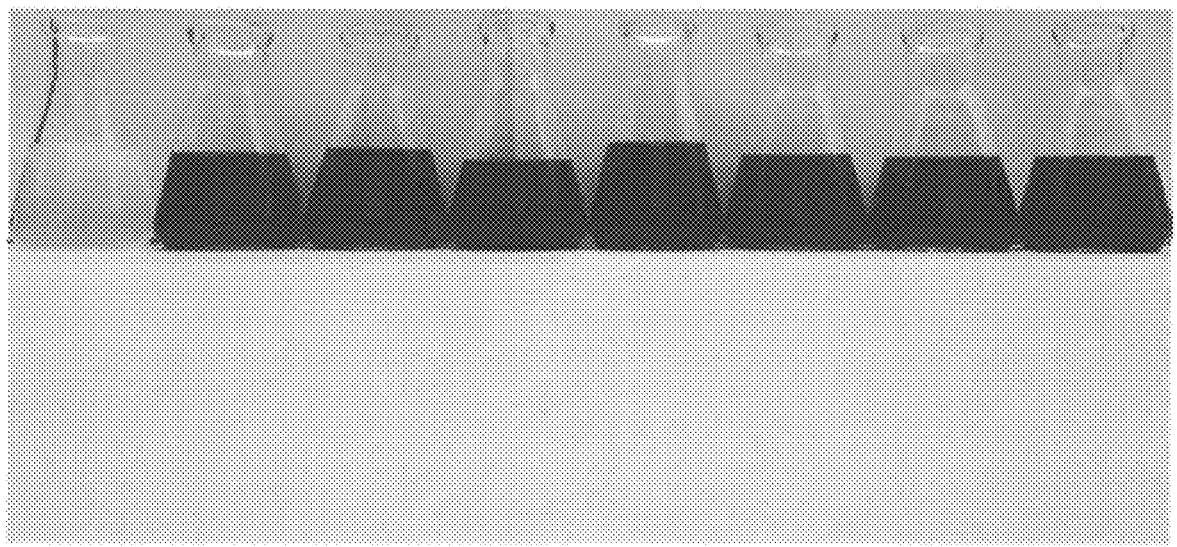
FIG. 3 shows unfiltered solutions of the dosage forms in 190 proof ethanol after shaking at 250 rpm for 3 hours.
Figure 4:
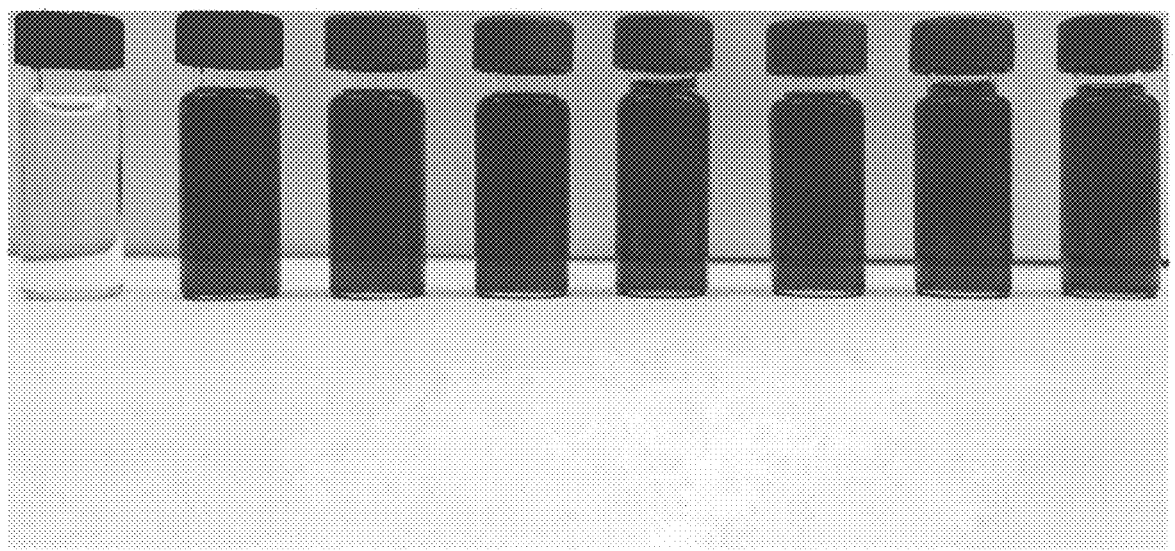
FIG. 4 shows syringe-filtered solutions of the dosage forms in 190 proof ethanol after shaking at 250 rpm for 3 hours.
Figure 5:
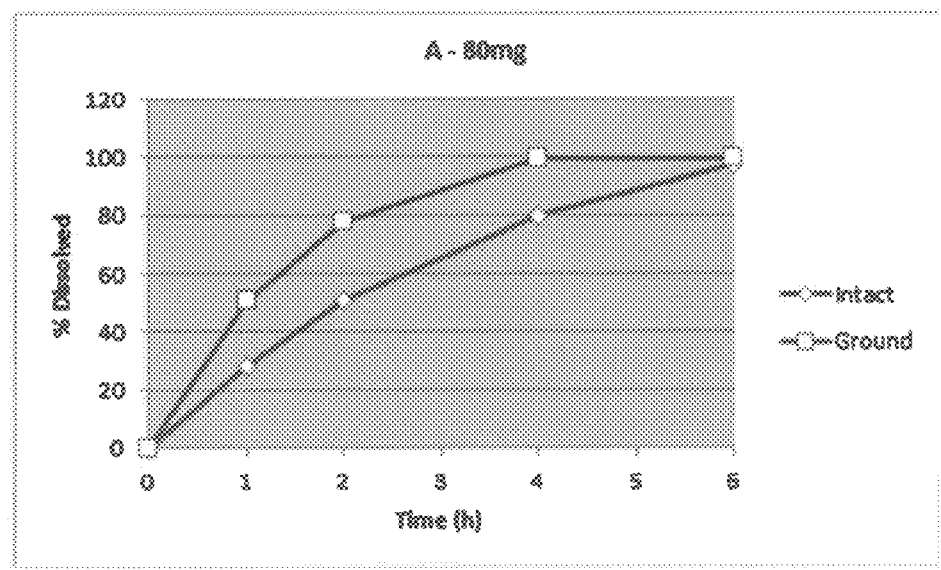
FIG. 5 shows the difference in dissolution between an intact and ground extended release, abuse deterrent capsule containing 80 mg of active.
Figure 6:
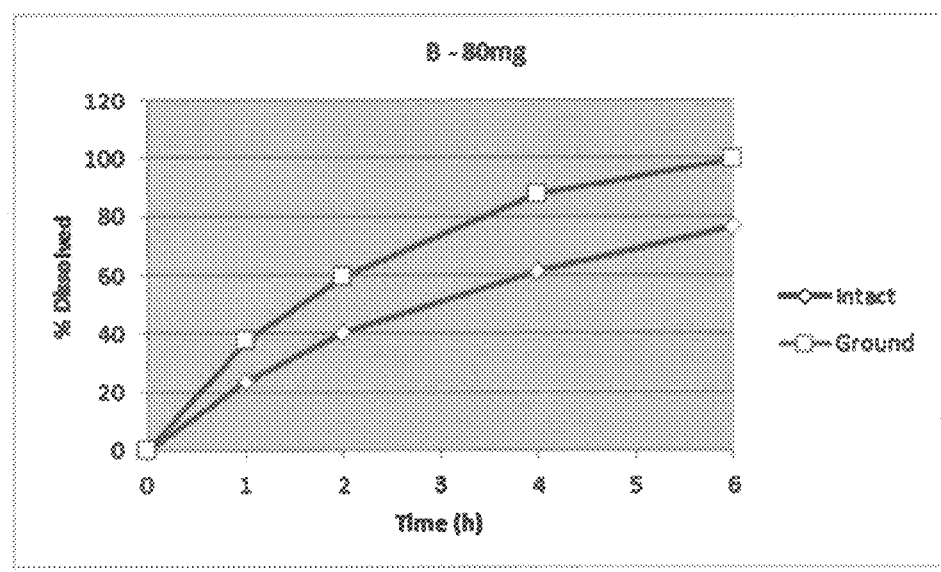
FIG. 6 shows the difference in dissolution between an intact and ground extended release, abuse deterrent capsule containing 80 mg of active.
Figure 7:
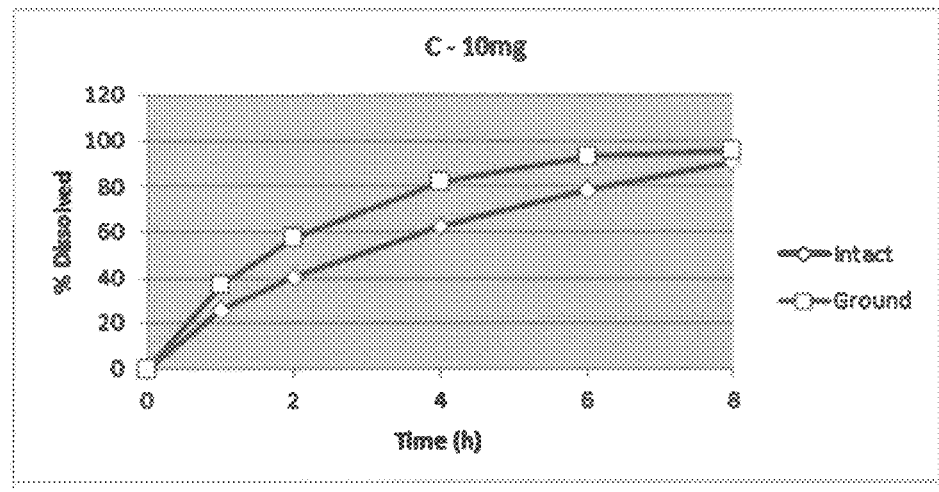
FIG. 7 shows the difference in dissolution between an intact and ground extended release, abuse deterrent capsule containing 10 mg of active.
Figure 8:
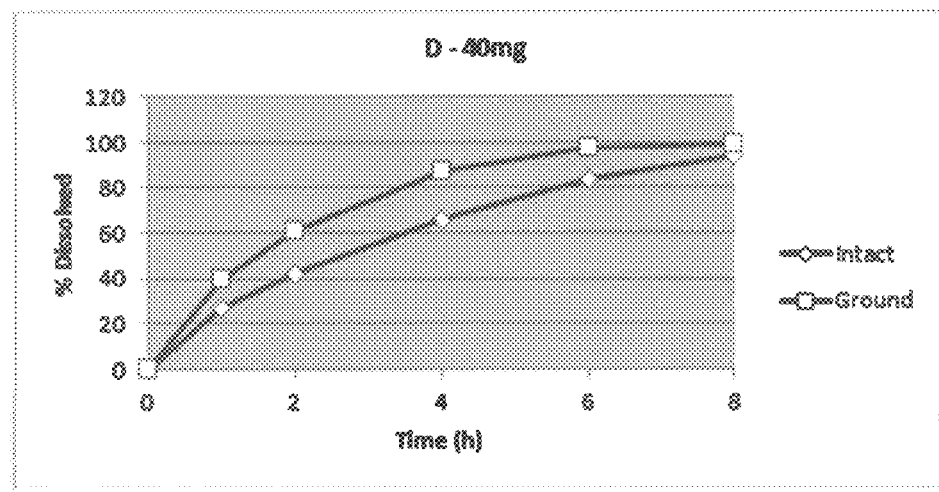
FIG. 8 shows the difference in dissolution between an intact and ground extended release, abuse deterrent capsule containing 40 mg of active.

A study is conducted to investigate the effect of dyes in the formulations of the present disclosure. Extraction products from whole formulations are visually inspected to determine abuse deterrence following alcohol extraction. Capsules are added to a flask containing 190 proof ethanol and shaken at 250 rpm for 3 hours. After 3 hours all capsule contents are fully dissolved. Solutions are filtered with a syringe filter and then visually analyzed for color intensity. FIGS. 3 and 4 show exemplary results of the tests.

The amount of dye present in the formulation can be an amount that produces an extract or a filtered extract using water, alcohol or a combination of both with a color that is greater than 0, or greater than 1, or greater than 2, or greater than 3 or greater than 4 on the visual scale disclosed, or similar scale. The amount of dye can vary depending on the formulation and components present. In some embodiments, the formulation can contain at least 0.1% dye, at least 0.2% dye, at least 0.3% dye, at least 0.4% dye, at least 0.5% dye, at least 0.6% dye, at least 0.7% dye, at least 0.8% dye, at least 0.9% dye, at least 1.0% dye, at least 1.5% dye, at least 2.0%, at least 3.0%, at least 4.0%, at least 5.0%, at least 6.0%, at least 7.0%, at least 8.0%, at least 9.0%, at least 10.0%, at least 11.0%, at least 12.0%, at least 13.0%, at least 14.0%, or any range of these values (e.g. between about 0.1% and about 1.0% dye).

Purity of the dosage form attainable in 190 proof ethanol and water was also tested. Additional formulations containing Gelucire® 50/13 (stearoyl polyoxylglyceride) were evaluated to determine the effect of the components on purity of the extractable API. The formulations were prepared using the same procedure of Example 1. The formulations are shown in Table 19 & 22. The purity data is shown in Tables 20 and 21. The composition of the present disclosure can reduce or minimize the purity of the resulting API extracted from the composition with alcohol, water or combinations thereof to a purity less than about 75%, 70%, 65%, 60%, 55%, 50%, 45%, 40%, 35%, 30%, 25%, 20%, 15%, or about 10%. These values can also define a range, such as about 20% to about 50%.

TABLE 20

Purity data for the Extended Release Liquid Fill Capsule Oxycodone Formulations

| | | Passes | | | % LC | | | | | |
|---|---|---|---|---|---|---|---|---|---|---|
| | | | | | Ethanol | | | Water | | 25° C. |
| Batch | Potency | Dissolution | Notes | 25° C. | 70° C. | 90° C. | 25° C. | 5° C. | (pH 1.2) |
| 36 | 40 | No | Gelucire ® 50/13 no PVP | 14 | N/A | 96 | 10 | 27 | 26 |
| 33 | 40 | Yes | Gelucire ® 50/13 PVP (12.5% w/w) | 26 | 108 | 177 | 62 | 42 | 56 |
| 47 | 80 | Yes | Gelucire ® 50/13 & 43/01 | 10 | N/A | 94 | 73 | 58 | 52 |

1 hour, unagitated, 5 mL/dosage unit

TABLE 21

Purity data for the Extended Release Liquid Fill Capsule Oxycodone Formulations

| | | Passes | | | % Purity | | | | | |
|---|---|---|---|---|---|---|---|---|---|---|
| | | | | | Ethanol | | | Water | | 25° C. |
| Batch | Potency | Dissolution | Notes | 25° C. | 70° C. | 90° C. | 25° C. | 5° C. | (pH 1.2) |
| 36 | 40 | No | Gelucire ® 50/13 no PVP | 9 | N/A | 15 | 23 | 25 | 20 |
| 33 | 40 | Yes | Gelucire ® 50/13 PVP (12.5% w/w) | 10 | 13 | 15 | 21 | 20 | 14 |
| 47 | 80 | Yes | Gelucire ® 50/13 & 43/01 | 27 | N/A | 50 | 61 | 57 | 56 |

Evaporated residue

In some embodiments, the formulation is homogenous and does not undergo any visible phase separation after all of the formulation components are combined. For example, in a formulation containing two components having drastically different HLB numbers, a visible phase separation between two portions of the formulation can occur. When a visible phase separation occurs, the formulation is no longer homogenous. A non-homogeneous formulation can result in a non-homogeneous dosage form. Similarly, a visible phase separation can also occur when the formulation has a high content of non-melting components. In formulations that cannot form a single phase, e.g., formulations that becomes saturated to the point of which the melt becomes a viscous paste, the formulation is no longer homogeneous. For example, formulations containing over 10% of PEG 35K can become non-homogenous.

Example 9—Extended Release ADF Oxycodone Hydrochloride Liquid Fill Capsules with Stearoyl Polyoxylglyceride Additional formulations containing stearoyl polyoxylglyceride were evaluated to determine the effect on release profiles. The formulations were prepared using the same procedure of Example 1. The formulations are shown in Table 22. The release profiles are shown in the Table 23.

TABLE 22

Oxycodone Hydrochloride liquid fill capsules.

| Component | Wt % 36 | Wt % 47 |
|---|---|---|
| Oxycodone | 14.55 | 29.09 |
| Stearoyl polyoxylglyceride | 79.36 | 17.32 |
| Glycerol esters of sat. C12-C18 fatty acids | 0 | 47.5 |
| Kollidon 90F (PVP) | 0 | 0 |
| PEG 3350 | 0 | 0 |
| Grey Dye Blend | 5.09 | 5.09 |
| Citric Acid | 1 | 1 |
| Active, mg | 40 | 80 |
| Capsule Fill Wt, mg | 275 | 275 |

TABLE 23

Dissolution testing of Oxycodone Hydrochloride liquid fill capsules (Average of 3 capsules)

| Formulation | 1 Hour | 2 Hour | 4 Hour | 6 Hour | 8 Hour |
|---|---|---|---|---|---|
| 36 | 25.98 | 43.93 | 72.57 | 88.49 | 95.55 |
| 47 | 33.12 | 49.33 | 70.47 | 84.19 | N/A |

Example 10—Extended Release ADF Oxycodone Hydrochloride Liquid Fill Capsules with HPMC and PEG 3350

Additional formulations containing stearoyl polyoxylglyceride, HPMC and PEG 3350 were evaluated to determine the effect on release profiles. The formulations were prepared using the same procedure of Example 1. The formulations are shown in Table 24. The release profiles and viscosity are shown in the Tables 25 and 26.

TABLE 24

Oxycodone Hydrochloride liquid fill capsules.

| Component | Wt % 37 | Wt % 38 | Wt % 39 | Wt % 40 | Wt % 41 | Wt % 42 | Wt % 43 | Wt % 44 | Wt % 45 | Wt % 46 |
|---|---|---|---|---|---|---|---|---|---|---|
| Oxycodone | 5 | 5.405 | 16.00 | 14.55 | 14.55 | 14.55 | 16.00 | 16.00 | 16.00 | 16.00 |
| Stearoyl polyoxylglyceride | 32 | 31.97 | 62.91 | 69.42 | 64.41 | 59.42 | 70.20 | 60.20 | 50.20 | 40.20 |
| HPMC | 15 | 16.22 | 0 | 0 | 0 | 0 | 0 | 0 | 0 | 0 |
| Kollidon 90F (PVP) | 0 | 0 | 15.0 | 12.49 | 12.49 | 12.49 | 0 | 0 | 0 | 0 |
| PEG 3350 | 40 | 37.84 | 0 | 0 | 5.0 | 10.0 | 10.0 | 20.0 | 30.0 | 40.0 |
| Grey Dye Blend | 7 | 7.565 | 5.09 | 2.55 | 2.55 | 2.55 | 2.80 | 2.80 | 2.80 | 2.80 |
| Citric Acid | 1 | 1 | 1 | 1 | 1 | 1 | 1 | 1 | 1 | 1 |
| Active, mg | 10 | 10 | 80 | 80 | 80 | 80 | 80 | 80 | 80 | 80 |
| Capsule Fill Wt, mg | 200 | 185 | 500 | 550 | 550 | 550 | 500 | 500 | 500 | 500 |

TABLE 25

Dissolution testing of Oxycodone Hydrochloride liquid fill capsules (Average of 3 capsules)

| Formulation | 1 Hour | 2 Hour | 3 Hour | 4 Hour | 12 Hour |
|---|---|---|---|---|---|
| 37 | 31.133 | 48.032 | 63.325 | 75.886 | 101.048 |
| 38 | 30.159 | 47.992 | 61.080 | N/A | N/A |

TABLE 26

Viscosity of Oxycodone Hydrochloride liquid fill capsules

| Formulation | Potency (mg) | % Melting Components | % Non-Melting Components | Viscosity (cP) @ 75° C. |
|---|---|---|---|---|
| 31 | 10 | 75.00 | 25.00 | 1190 |
| 32 | 20 | 71.00 | 29.00 | 1490 |
| 33 | 40 | 71.96 | 28.04 | 1640 |
| 34 | 80 | 83.00 | 17.00 | 408 |
| 35 | 80 | 83.00 | 17.00 | 342 |
| 37 | 10 | 79.00 | 21.00 | 1520 |
| 38 | 10 | 77.38 | 22.62 | 2080 |
| 39 | 80 | 68.00 | 32.00 | 4010 |
| 40 | 80 | 71.96 | 28.04 | 1805 |
| 41 | 80 | 71.96 | 28.05 | 1910 |
| 43 | 80 | 83.00 | 17.00 | 465 |
| 45 | 80 | 83.00 | 17.00 | 502 |
| 46 | 80 | 83.00 | 17.00 | 520 |

The % Melting Components refers to the components that melt at a relatively low temperature, such as below about 70° C. (or as otherwise provided herein), and can include the controlled release agent, PEG, and dye blend. The % Non-Melting Components refers to the components that melt at a relatively higher temperature, such as above about 70° C. (or as otherwise provided herein), and can include the API, HPMC and PVP.

We claim:

1. An extended release, abuse deterrent capsule consisting of:
   (a) an opioid susceptible to abuse, wherein said opioid is about 0.5-15 wt % of said capsule;
   (b) a hydrophilic controlled release agent that is stearoyl polyoxylglyceride, and is from about 50% to about 80% of the capsule,
   (c) a second agent that has a melting temperature greater than or equal to about 100° C. and is selected from the group consisting of hydroxypropyl methylcellulose, and polyvinylpyrrolidone, wherein the second agent is from about 5% to about 30 wt % of the capsule,
   (d) optionally, a dye, and/or polyethylene glycol (PEG), and,
   (e) optionally, one or more antioxidants or preservatives selected from the group consisting of: citric acid, ascorbic acid, ascorbyl palmitate, butylated hydroxyanisole, butylated hydroxytoluene, erythorbic acid, hypophosphorous acid, lactobionic acid, monothioglycerol, potassium metabisulfite, propyl gallate, racemethionine, sodium bisulfite, sodium formaldehyde sulfoxylate, sodium metabisulfite, sodium sulfite, sodium thiosulfate, stannous chloride, sulfur dioxide, and tocopherols,
   wherein said capsule has an extended release profile of said opioid characterized by: about 20-40% release by 1 hour, and 55-75% release by 4 hours.

2. The capsule of claim 1, wherein the opioid is selected from the group consisting of hydrocodone, oxycodone HCl, and hydromorphone HCl.

3. The capsule of claim 1, wherein the opioid is oxycodone HCl.

4. The capsule of claim 1, wherein the opioid is between about 10 mg and about 40 mg.

5. The capsule of claim 1, wherein the second agent is polyvinylpyrrolidone.

6. The capsule of claim 1, wherein the dye is present in said capsule.

7. The capsule of claim 6, wherein the dye is selected from the group consisting of FD&C Blue #1, FD&C Yellow #6, and FD&C Red #40.

8. The capsule of claim 7, wherein the dye reduces abuse via extracting and injecting.

9. The capsule of claim 1, wherein the opioid is about 2.5 wt %, and up to 15 wt % of the capsule.

10. The capsule of claim 1, wherein the capsule is prepared by filling a capsule body with a heated homogenized suspension with the opioid, the controlled release agent, and the second agent.

11. The capsule of claim 1, wherein the capsule is a 175 mg, 200 mg, 250 mg, or 275 mg capsule.

12. The capsule of claim 1, wherein the contents of the capsule are solid at 40° C./75% relative humidity.

13. The capsule of claim 1, wherein the composition of (a)-(e) has a processable viscosity of less than about 1800 cP at 75° C.

14. An extended release, abuse deterrent capsule consisting of:
  (a) an opioid susceptible to abuse selected from the group consisting of hydrocodone, oxycodone HCl, and hydromorphone HCl, wherein said opioid is about 0.5-15 wt % of said capsule;
  (b) stearoyl polyoxylglyceride having a melting temperature less than or equal to about 70° C.,
  (c) polyvinylpyrrolidone having a melting temperature greater than or equal to about 100° C.,
  (d) optionally, a dye, and/or polyethylene glycol (PEG), and,
  (e) optionally, one or more antioxidants or preservatives selected from the group consisting of: citric acid, ascorbic acid, ascorbyl palmitate, butylated hydroxyanisole, butylated hydroxytoluene, erythorbic acid, hypophosphorous acid, lactobionic acid, monothioglycerol, potassium metabisulfite, propyl gallate, racemethionine, sodium bisulfite, sodium formaldehyde sulfoxylate, sodium metabisulfite, sodium sulfite, sodium thiosulfate, stannous chloride, sulfur dioxide, and tocopherols,
  wherein said capsule has an extended release profile of said opioid characterized by: about 20-40% release by 1 hour, and 55-75% release by 4 hours.

15. The capsule of claim 14, wherein the stearoyl polyoxylglyceride is from about 50 wt % to about 80 wt % of the capsule and the polyvinylpyrrolidone is from about 5 wt % to about 30 wt % of the capsule.

16. The capsule of claim 14, wherein the hydrocodone, oxycodone HCl, or hydromorphone HCl is from about 2.5 wt % to about 15 wt %, the stearoyl polyoxylglyceride is from about 55 wt % to about 80 wt % of the capsule and the polyvinylpyrrolidone is from about 10 wt % to about 25 wt % of the capsule.

17. The capsule of claim 14, wherein the purity of an extraction product from the capsule using water is less than about 25%.

18. The capsule of claim 14, wherein the purity of an extraction product from the capsule using ethanol is less than about 25%.

* * * * *